(12) United States Patent
Omar et al.

(10) Patent No.: US 11,479,536 B1
(45) Date of Patent: *Oct. 25, 2022

(54) ARYLACETAMIDES AS AMP-ACTIVATED PROTEIN KINASE INHIBITORS AND THEIR USE FOR TREATMENT OF BREAST CANCER

(71) Applicant: King Abdulaziz University, Jeddah (SA)

(72) Inventors: Abdelsattar M. Omar, Jeddah (SA); Mohammad Imran Khan, Jeddah (SA); Moustafa Elsayed El-Araby, Jeddah (SA); Mahmood Hassan Dalhat, Jeddah (SA); Mohammed Razeeth S. Mohammed, Jeddah (SA); Majed Abdullah A. Alharbi, Jeddah (SA); Yosra A. Muhammad, Jeddah (SA); Hani Mohammed Z. Choudhry, Jeddah (SA); Amer Hamzah O. Asseri, Jeddah (SA); Khadijah A. Mohammad, Jeddah (SA); Maan T. Khayat, Jeddah (SA)

(73) Assignee: KING ABDULAZIZ UNIVERSITY, Jeddah (SA)

(*) Notice: Subject to any disclaimer, the term of this patent is extended or adjusted under 35 U.S.C. 154(b) by 0 days.

This patent is subject to a terminal disclaimer.

(21) Appl. No.: 17/730,885

(22) Filed: Apr. 27, 2022

(51) Int. Cl.
*C07D 213/75* (2006.01)
*C07D 295/088* (2006.01)
*C07C 235/56* (2006.01)
*C07D 307/68* (2006.01)
*C07D 213/81* (2006.01)
*C07D 213/82* (2006.01)

(52) U.S. Cl.
CPC ........ *C07D 295/088* (2013.01); *C07C 235/56* (2013.01); *C07D 213/75* (2013.01); *C07D 213/81* (2013.01); *C07D 213/82* (2013.01); *C07D 307/68* (2013.01)

(58) Field of Classification Search
CPC .......................... C07D 213/75; C07C 235/56
See application file for complete search history.

(56) References Cited

U.S. PATENT DOCUMENTS

| | | | | |
|---|---|---|---|---|
| 10,988,439 | B2 * | 4/2021 | El-Araby | C07C 233/64 |
| 11,136,288 | B2 * | 10/2021 | El-Araby | C07C 233/64 |
| 11,142,493 | B1 * | 10/2021 | El-Araby | C07D 295/192 |
| 11,214,537 | B2 * | 1/2022 | El-Araby | C07C 311/21 |
| 11,312,680 | B2 * | 4/2022 | El-Araby | A61P 35/00 |
| 11,325,885 | B2 * | 5/2022 | El-Araby | A61P 35/00 |

* cited by examiner

*Primary Examiner* — Golam M Shameem
(74) *Attorney, Agent, or Firm* — WCF IP

(57) ABSTRACT

Therapeutic compounds containing an arylacetamide core pending N-benzyl group. Also described are pharmaceutical compositions incorporating the therapeutic compounds and a method for inhibiting AMP-activated kinase (AMPK) and their use thereof for treating breast and pancreatic cancer with the specified compounds.

4 Claims, 9 Drawing Sheets

|  | IC$_{50}$ (μM) HL-60 (Leukemia)[1] | IC$_{50}$ (μM) MCF7 (Breast) | AMPK phosphoprotein inhibition % (Concentration μM)* |
|---|---|---|---|
| KAC-12 | 1.62 | 47.72 | 12.9% (4 μM) |
| MAK-1 | 3.27 | 0.490 | 61.8% (6 μM) |
| MAK-6 | 6.24 | 0.705 | 92.1% (8 μM) |

* Tested on HL60 cell line using R&D phosphoproteome profiler (See Methodology Section for details)

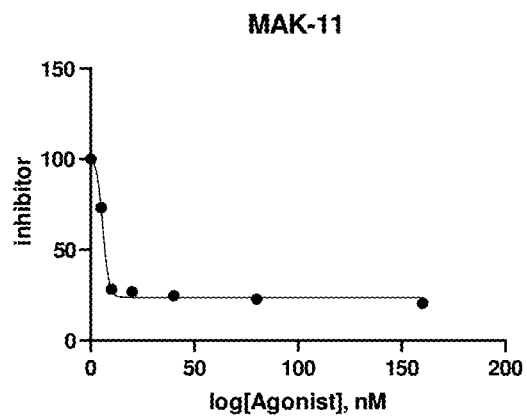
FIGURE 6C
| Compound Code | MCF7 | | T47D | |
|---|---|---|---|---|
| | IC$_{50}$ (μM) | SEM | IC$_{50}$ (μM) | SEM |
| MAK-1 | 23.81 | 0.160 | 13.90 | 0.095 |
| MAK-6 | 22.87 | 0.245 | 7.29 | 0.085 |
| MAK-11 | 19.58 | 0.525 | 3.72 | 0.030 |
FIGURE 7
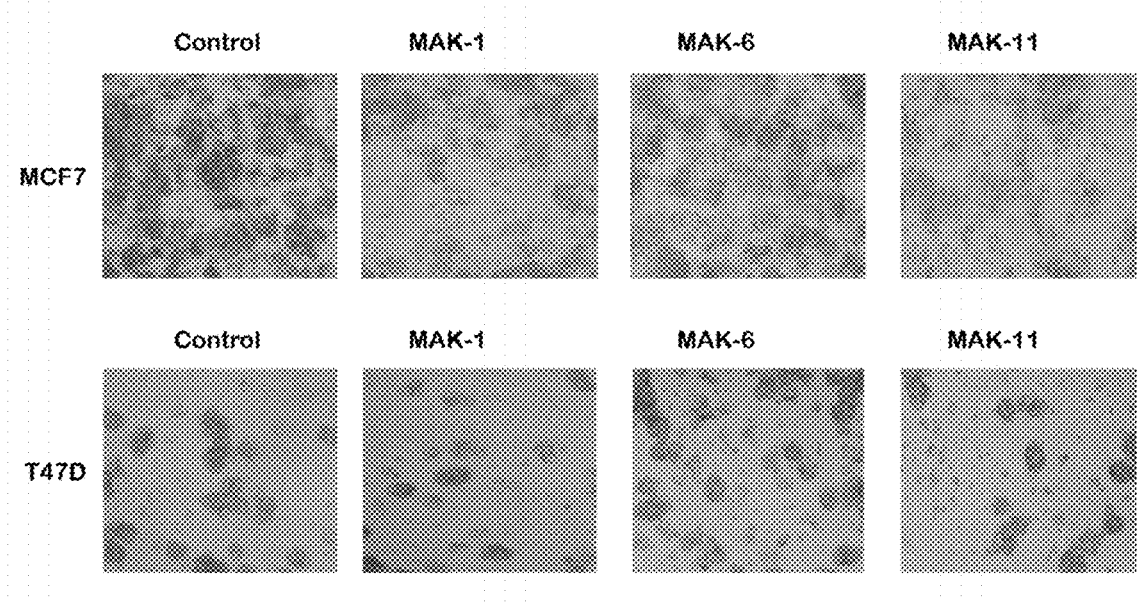
Figure 8

| Compound Code | MCF7 | | T47D | |
|---|---|---|---|---|
| | IC$_{50}$ (µM)[a] | SEM[b] | IC$_{50}$ (µM) | SEM |
| *MAK-1* | 0.490 | 0.020 | 1.240 | 0.010 |
| *MAK-2* | 0.006 | 0.001 | 1.145 | 0.005 |
| *MAK-3* | 0.325 | 0.095 | 0.00095 | 0.00005 |
| *MAK-4* | 0.225 | 0.095 | 0.185 | 0.025 |
| *MAK-5* | 0.735 | 0.085 | 0.160 | 0.010 |
| *MAK-6* | 0.705 | 0.015 | 0.0012 | 0.0002 |
| *MAK-7* | 0.820 | 0.070 | 0.900 | 0.010 |
| *MAK-8* | 0.395 | 0.025 | 0.135 | 0.035 |
| *MAK-9* | 0.320 | 0.010 | 0.400 | 0.020 |
| *MAK-10* | 0.225 | 0.025 | 0.435 | 0.015 |
| *MAK-11* | 0.148 | 0.002 | 0.097 | 0.003 |

| Comp. No. | Max. aq. Sol. (μM) | Stability HLM[1] $t_{1/2}$ (min)[2] | Mic. Ctrl. Human % @60 min[3] | CYP3A4 $IC_{50}$ (μM) | CYP2D6 $IC_{50}$ (μM) | CYP2C9 $IC_{50}$ (μM) | Mouse Plasma Stability $t_{1/2}$ (min) | Mouse PPB (% free) |
|---|---|---|---|---|---|---|---|---|
| MAK-1 | 9.4 | 35.6 | 99 | >10 | >10 | >10 | >300 | 8.3 |
| MAK-6 | 3.7 | >60 | 125 | >10 | >10 | >10 | >300 | 8.7 |

[1]HLM = Human Liver Microsomes

[2]Assay carried out in presence of NADPH.

[3]Assay carried out without NADPH; percent remaining after 60 min incubation.

FIGURE 13

| Compound Code | HSF[1] inhibition | | Selectivity on MCF7 cancer cells[2] |
|---|---|---|---|
| | $IC_{50}$ (μM) | SEM | |
| MAK-1 | 3.65 | 0.034 | 7.45 |
| MAK-6 | >100 | | >100 |
| MAK-11 | >100 | | >100 |

[1]HSF, human skin fibroblast

[2]Selectivity on cancer cells = $IC_{50}$ (HSF)/$IC_{50}$ (MCF7)

FIGURE 14

ARYLACETAMIDES AS AMP-ACTIVATED PROTEIN KINASE INHIBITORS AND THEIR USE FOR TREATMENT OF BREAST CANCER

FIELD OF INVENTION

The invention is generally related to agents with strong inhibitory activities against AMP-activated kinase (AMPK). Structurally, these compounds embody N-benzylacetamide derivatives with 2-(4-arylcarbonylaminoaryl) substitutions. The compounds are suitable for treating malignant tumors that have cancer cells became dependent on AMPK for their proliferation. The compounds might be used alone (monotherapy), or in combination with existing drugs.

BACKGROUND

Cancer is a group of diseases characterized by rapid, uncontrolled cell proliferation that eventually leads to the acquisition of metastatic properties [1]. The incidence of cancer is increasing globally, and the estimates show that 19.3 million new patients were diagnosed with cancer in 2020 [2]. Female breast cancer accounts for 11.7% of the new cancer cases to make it as the most commonly diagnosed type of cancer in the world [2]. Although the great advancements in the scientific technologies have substantially improved the conceptual understanding of cancer biology during the past decade, cancer still ranks as one of the leading causes of death in the world [2]. This persistent high mortality rate in cancer raises the demand for new strategies to target the uncontrolled cell growth and promote apoptosis in cancer cells.

AMP-activated Protein Kinase (AMPK), which is a key regulator for energy homeostasis, has recently emerged as a new target that can be modulated in cancer cells [3]. Structurally, AMPK exists in heterotrimeric complexes composed of catalytic subunit (a) and regulatory subunits (β and γ). This kinase is usually activated in response to the reduction in the ATP: AMP or ATP:ADP ratios to restore energy homeostasis through inhibiting anabolic processes that consume ATP including fatty acid synthesis (via Acetyl coenzyme A carboxylase (ACC1)), glycogen (via glycogen synthase (GYS)) and proteins (via mechanistic target of rapamycin complex 1 (mTORC1)). AMPK also stimulates catabolic processes leading to generation of ATP (i.e. promoting glucose uptake, fatty acid oxidation, and mitochondrial biogenesis) [4]. The activity of AMPK is also regulated by several mechanisms: a) The phosphorylation state of the conserved threonine residue 172 (Thr172) by upstream kinases, Liver Kinase B1 (LKB1) and $Ca^{2+}$/Calmodulin-dependent Kinase (CaMKK2); b) Glucose deprivation through nucleotide ratio-dependent (ATP:AMP, ATP:ADP) and -independent manners. The active form of AMPK was found to improve glucose uptake through Glucose Transporters 1 and 4 (GLUT1 and GLUT4) as well as stimulation of glycolysis and fatty acid oxidation via inhibition of ACC2. The AMPK-dependent inhibition of ACC1 and ACC2 are important mechanisms for redox regulation that maintains NADPH levels [4]. AMPK has long been regarded as a mediator for the tumor suppression activity of its upstream regulator Liver Kinase B1 (LKB1) [5] (See, for example, FIG. 1).

Therefore, many AMPK activators have been designed and extensively studied for the prevention and treatment of cancer. The significant reduction in the risk of malignancy in type 2 diabetes patients who are under treatment with metformin, a known AMPK activator, suggested that AMPK upregulation is beneficial in preventing the development of cancer. However, metformin's effect occurs before the initiation of the malignant disease. Metformin also was found to reduce the likelihood of relapse of tumors after commencement of the chemotherapy [6-8]. Some other AMPK activators have been developed through preclinical models, and a handful of them have already reached clinical trials in the area of cancer chemotherapy [9]. Recently, additional developments unfolded in the area of AMPK research when several studies pointed out that, under metabolic stress conditions, AMPK activators (metformin) suppress tumor growth by downregulating AMPK rather than through its activation. Evidences were given that cancer cells lacking LKB1/AMPK signaling are more prone to undergo apoptosis than cancer cells that possess functional LKB1/AMPK pathway [5, 10]. This paradoxical effect for AMPK activation has recently raised concerns about the feasibility of AMPK activation strategy to exert an effective anticancer effect. In contrast, growing scientific evidences have suggested that AMPK inhibition is the right path for the development of novel anticancer agents [11-13]. Recent studies provided evidences that AMPK could serve as a tumor promoter after the development of the disease by activating pathways to help immortal behavior of cancer cells (FIG. 1) [14-18]. A recent study has reported a strong correlation between elevated expression of AMPK and reduced median survival time in patients diagnosed with pancreatic cancer, and the inhibition of AMPK activity resulted in cell cycle arrest and apoptosis in two pancreatic cancer cell lines [19]. An additional study has found that AMPK is upregulated in dormant breast cancer cells, and this upregulation is key for the survival of these cells [20]. The authors have also mentioned that the inhibition of AMPK promoted the eradication of the dormant breast cancer cells. Under metabolic stress, AMPK maintains NADPH levels to facilitate redox balance when NADPH generation from Pentose Phosphate Pathway is impaired [21, 22]. This effect in turn helps cancer cells adapt to survive in the harsh tumor microenvironment, indicating that AMPK inhibition can induce apoptosis in cancer cells [19, 23, 24].

To date, the only two AMPK inhibitors that have been reported in the literature are Dorsomorphin and Sunitinib. However, the involvement of AMPK inhibition in their cytotoxic activities is not clear since both drugs suppress the activity of several other kinases with much more potency [25-27]. In addition, Dorsomorphin was shown to exert proapoptotic activity either indirectly by sensitizing cancer cells to anticancer therapies or directly through modulating lipid metabolism in different cell lines including breast cancer cells [28-31]. Although AMPK inhibiting concentrations were used in these studies, the anticancer effects of Dorsomorphin were attributed to AMPK-independent mechanisms. Therefore, we aimed in this study to design novel compounds to selectively inhibit AMPK and test their activity against breast cancer cells.

The inventors embarked on investigations of a previously disclosed compound KAC-12 (see, structure on FIG. 2) [El-Araby, M. E.; Omar, A.; Khayat, M. T.; Malebari, A. M.; Ahmed, F. Shah, D.; Safo, M. Method for making anticancer compounds. U.S. Pat. No. 11,214,537 B2, Jan. 4, 2022, El-Araby, M. E.; Omar, A.; Khayat, M. T.; Malebari, A. M.; Ahmed, F. Shah, D.; Safo, M. Pharmaceutical Composition for Treating Cancer. U.S. Pat. No. 11,142,493 B1, Oct. 19, 2021. El-Araby, M. E.; Omar, A.; Khayat, M. T.; Malebari, A. M.; Ahmed, F. Shah, D.; Safo, M. Method of Treating a Patient Having Cancer. U.S. Pat. No. 11,136,288 B2, Oct. 5, 2021, El-Araby, M. E.; Omar, A.; Khayat, M. T.; Malebari, A. M.; Ahmed, F. Shah, D.; Safo, M. Compounds, Pharmaceutical Compositions Thereof and Methods of Treating Cancer. U.S. Pat. No. 10,988,439 B2, Apr. 27, 2021. El-Araby, M. E.; Omar, A.; Khayat, M. T.; Malebari, A. M.; Ahmed, F. Shah, D.; Safo, M. Amide Group-Containing Compounds and Use for Cancer Treatment. U.S. Pat. No. 10,844,007 B1, Nov. 24, 2020] which was noticed that it slightly downregulated the activated AMPK signal (phosphoprotein) by 13% [Omar, A. M.; Khayat, M. T.; Ahmed, F.; Muhammad, Y. A.; Malebari, A. M.; Ibrahim, S. M.; Khan, M. I.; Shah, D. K.; Childers, W. E. and El-Araby, M. E. SAR Probing of KX2-391 Provided Analogues with Juxtaposed Activity Profile Against Major Oncogenic Kinases. 2022, Frontiers in Oncology, Accepted, In Press].

SUMMARY

Cytotoxic assays of KAC-12 (see FIG. 3) revealed that it had weak activities on breast cancer (MCF7 cell lines) with $IC_{50}$ in MCF7 cell lines=47.7 µM. However, the compound showed higher toxic activities on leukemia cell lines (FIG. 3).

Although the effect of KAC-12 (FIG. 2), a compound belonging to 4-(acylamino)phenyl-N-benzylacetamide scaffold, was not strong inhibitor of AMPK, but it met our high interest in the target. Therefore, we designed derivatives to increase activities against AMPK and therefore, bring higher therapeutic benefits against breast cancer. We synthesized several analogues of KAC-12 hoping to increase both AMPK inhibition and, subsequently, breast cancer cell line inhibition. We tested two of these analogues (MAK-1 and MAK-6) and they showed comparable activities against leukemia cell lines HL60 to that of KAC-12 ($IC_{50}$ values at 3.27±0.15 µM and 6.24±3.3 for MAK-1 and MAK-12, respectively) (FIG. 3). Using lysates of treated HL-60 cells, the effect on MAK-1 and MAK-6 were tested for their inhibition of AMPK signal at concentrations of 6 µM and 8 µM, respectively. This test (undisclosed here) was performed by detecting the intensity of antibody to the phospho-antigen [Omar, A. M.; Khayat, M. T.; Ahmed, F.; Muhammad, Y. A.; Malebari, A. M.; Ibrahim, S. M.; Khan, M. I.; Shah, D. K.; Childers, W. E. and El-Araby, M. E. SAR Probing of KX2-391 Provided Analogues with Juxtaposed Activity Profile Against Major Oncogenic Kinases. 2022, Frontiers in Oncology, Accepted, In Press]. Surprisingly, both MAK-1 and MAK-6 caused a profound decrease of phospho-protein AMPK existence by 61.8% and 92.1%, respectively. In as much as the result was exciting to us, but could not be correlated to a contribution the anticancer activities against the leukemic cell lines because the AMPK is not significantly overexpressed in HL60 cell line and therefore, it does not depend on this factor in their proliferation. We turned our attention to breast cancer cell lines because AMPK over expression is strongly implicated in the growth of this type of tumors. We found that the cytotoxic activities of the two new derivatives MAK-1 and MAK-6 well correlates with their AMPK inhibition activities on HL60 cell lines [El-Araby, M. E.; Omar, A.; Khayat, M. T.; Malebari, A. M.; Ahmed, F. Shah, D.; Safo, M. Method for making anti-cancer compounds. U.S. Pat. No. 11,214,537 B2, Jan. 4, 2022, El-Araby, M. E.; Omar, A.; Khayat, M. T.; Malebari, A. M.; Ahmed, F. Shah, D.; Safo, M. Pharmaceutical Composition for Treating Cancer. U.S. Pat. No. 11,142, 493 B1, Oct. 19, 2021. El-Araby, M. E.; Omar, A.; Khayat, M. T.; Malebari, A. M.; Ahmed, F. Shah, D.; Safo, M. Method of Treating a Patient Having Cancer. U.S. Pat. No. 11,136,288 B2, Oct. 5, 2021, El-Araby, M. E.; Omar, A.; Khayat, M. T.; Malebari, A. M.; Ahmed, F. Shah, D.; Safo, M. Compounds, Pharmaceutical Compositions Thereof and Methods of Treating Cancer. U.S. Pat. No. 10,988,439 B2, Apr. 27, 2021. El-Araby, M. E.; Omar, A.; Khayat, M. T.; Malebari, A. M.; Ahmed, F. Shah, D.; Safo, M. Amide Group-Containing Compounds and Use for Cancer Treatment. U.S. Pat. No. 10,844,007 B1, Nov. 24, 2020]. These exciting results were utilized to start target-based discovery of new anticancer agents that target AMP-activated kinase (AMPK).

An aspect of the invention pertains to new compounds defined by the generic formula

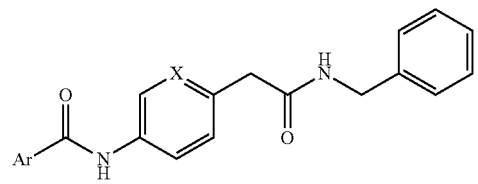

where X=CH, N,

Ar in some cases is

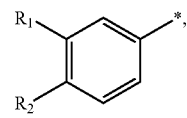

where $R_1$ and $R_2$ are the same or independently halogen or methoxy or

Z—$(CH_2)$n-Y—*,

Y=$CH_2$, NH, O or s, n=1-3 and

Z=amine, alkylamino or cyclic amines such as morpholine, piperidine of pyrrolidine.

Exemplary compounds include

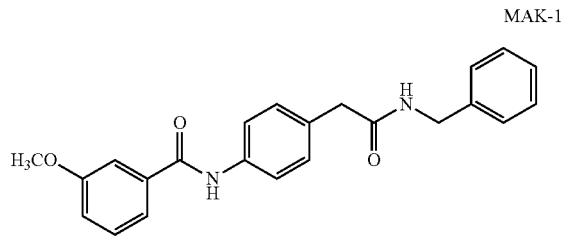

MAK-1

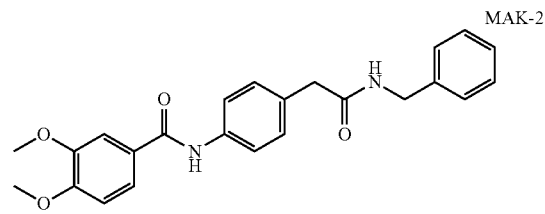

MAK-2

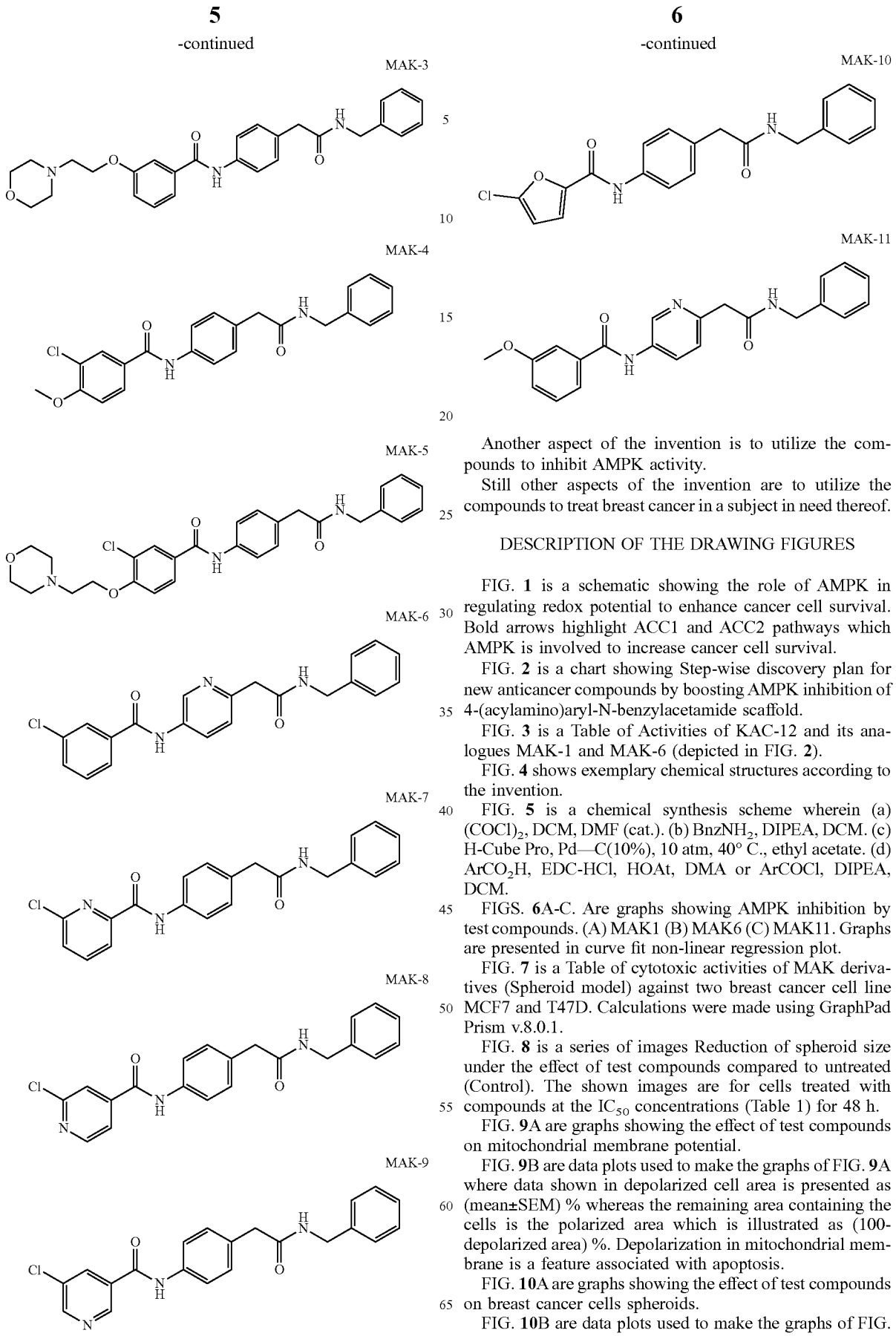

Another aspect of the invention is to utilize the compounds to inhibit AMPK activity.

Still other aspects of the invention are to utilize the compounds to treat breast cancer in a subject in need thereof.

DESCRIPTION OF THE DRAWING FIGURES

Figure 6A:
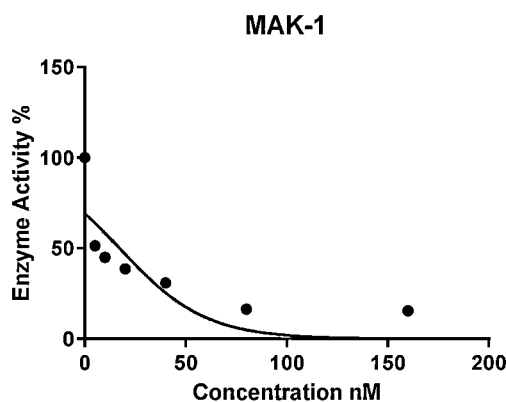
Figure 6B:
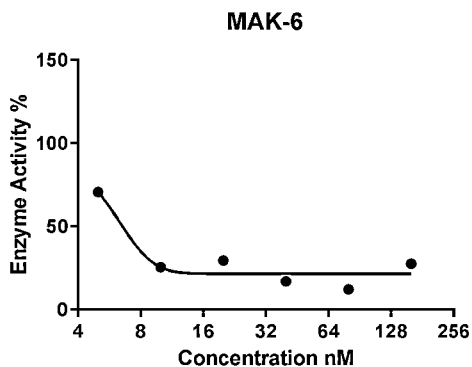

FIGS. 6A-C. Are graphs showing AMPK inhibition by test compounds. (A) MAK1 (B) MAK6 (C) MAK11. Graphs are presented in curve fit non-linear regression plot.

FIG. 7 is a Table of cytotoxic activities of MAK derivatives (Spheroid model) against two breast cancer cell line MCF7 and T47D. Calculations were made using GraphPad Prism v.8.0.1.

FIG. 8 is a series of images Reduction of spheroid size under the effect of test compounds compared to untreated (Control). The shown images are for cells treated with compounds at the $IC_{50}$ concentrations (Table 1) for 48 h.

Figure 9A:
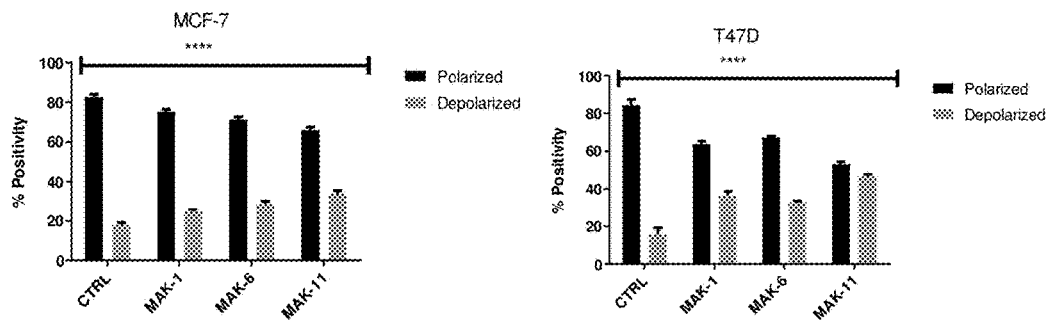

FIG. 9A are graphs showing the effect of test compounds on mitochondrial membrane potential.

Figure 9B:
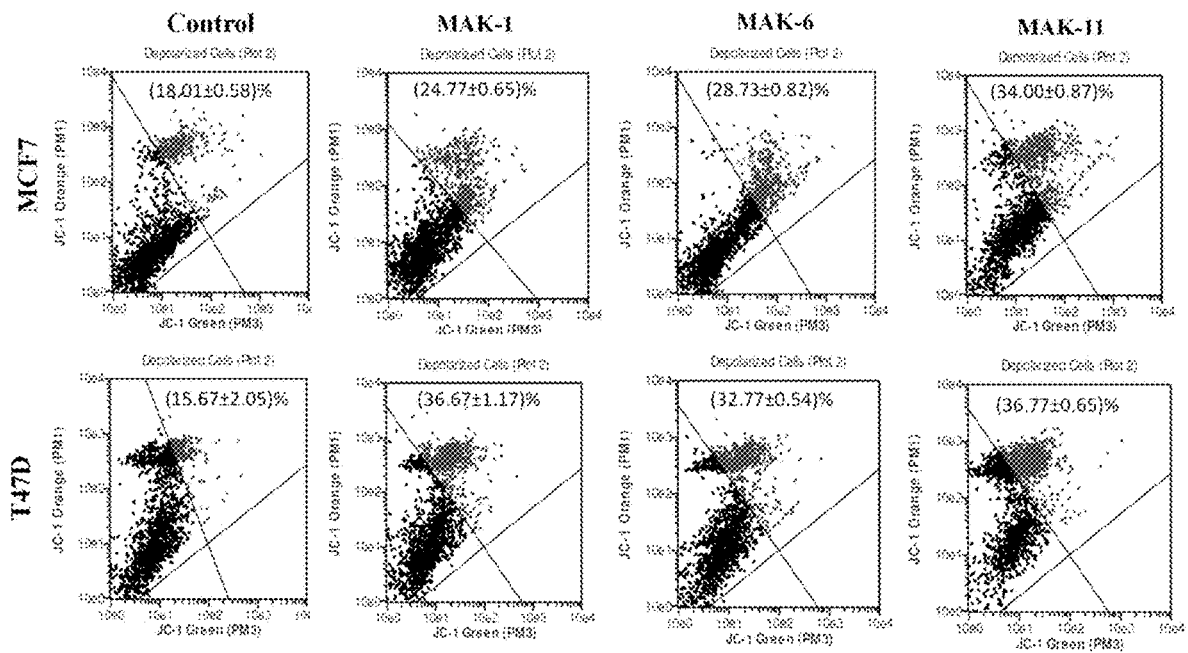

FIG. 9B are data plots used to make the graphs of FIG. 9A where data shown in depolarized cell area is presented as (mean±SEM) % whereas the remaining area containing the cells is the polarized area which is illustrated as (100-depolarized area) %. Depolarization in mitochondrial membrane is a feature associated with apoptosis.

Figure 10A:
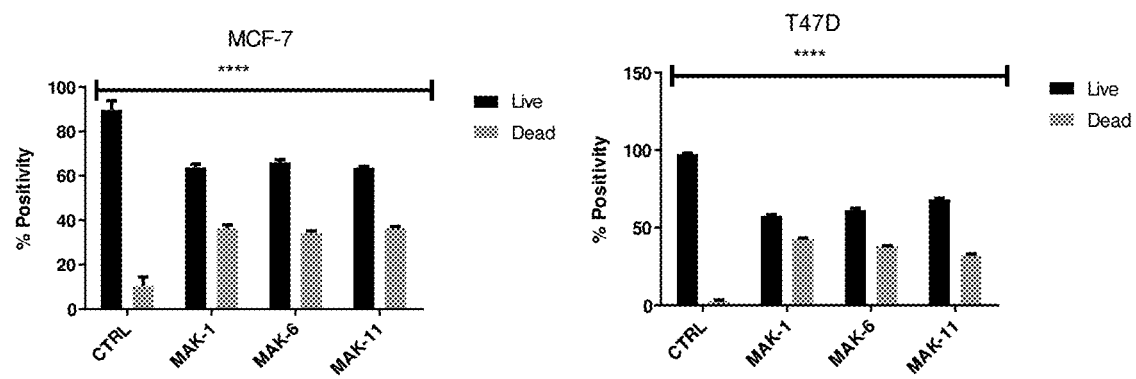

FIG. 10A are graphs showing the effect of test compounds on breast cancer cells spheroids.

Figure 10B:
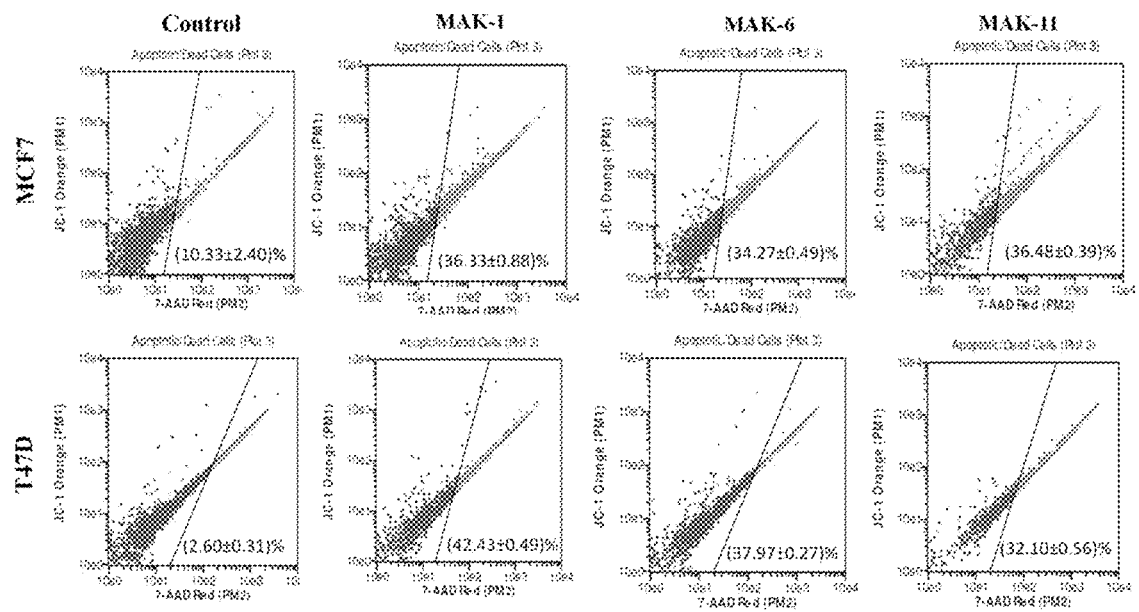

FIG. 10B are data plots used to make the graphs of FIG. 10A where data shown in dead cell area is presented as (mean±SEM) % whereas the remaining area containing the cells is the live cell area which is illustrated as (100-dead cell area) %. Increase in dead cell is related to efficacy of test compounds.

Figures 11, 12:
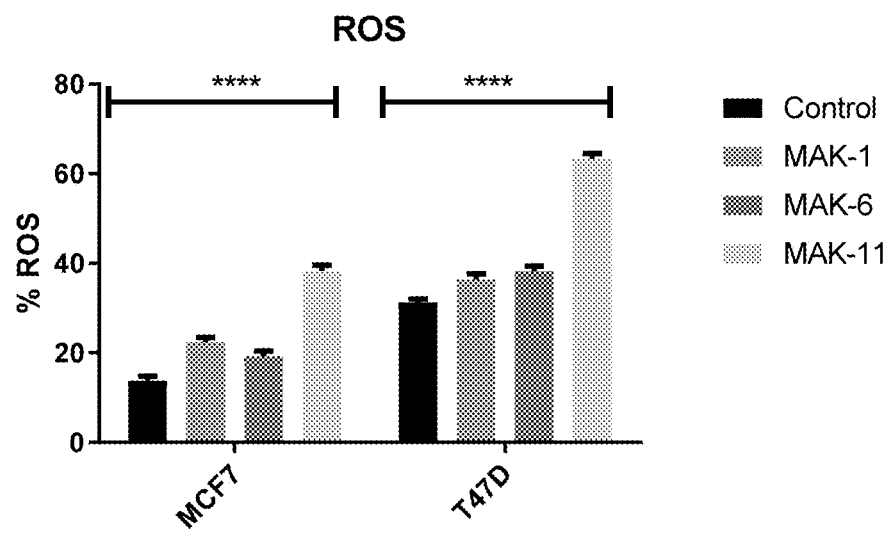

FIG. 11 is a bar graph showing ROS levels of test compounds. Error bars are represented in mean±SEM indicating percentage ROS levels and p=**** is extremely significant.

FIG. 12 is a Table of cytotoxic activities of MAK derivatives (Monolayer model) against two breast cancer cell line MCF7 and T47D. [a] $IC_{50}$, Concentration of the compound at which viability of cells are 50% of the control (untreated cells); [b]SEM, Standard Error of Means. Calculations were made using GraphPad Prism version 8.0.1.

FIG. 13 is a Table showing In vitro Physicochemical/ADME Data for MAK-1 and MAK-6.

FIG. 14 is a Table showing the effect of compounds on human skin fibroblasts (HSF) cell lines

DETAILED DESCRIPTION

Figures 3, 4:
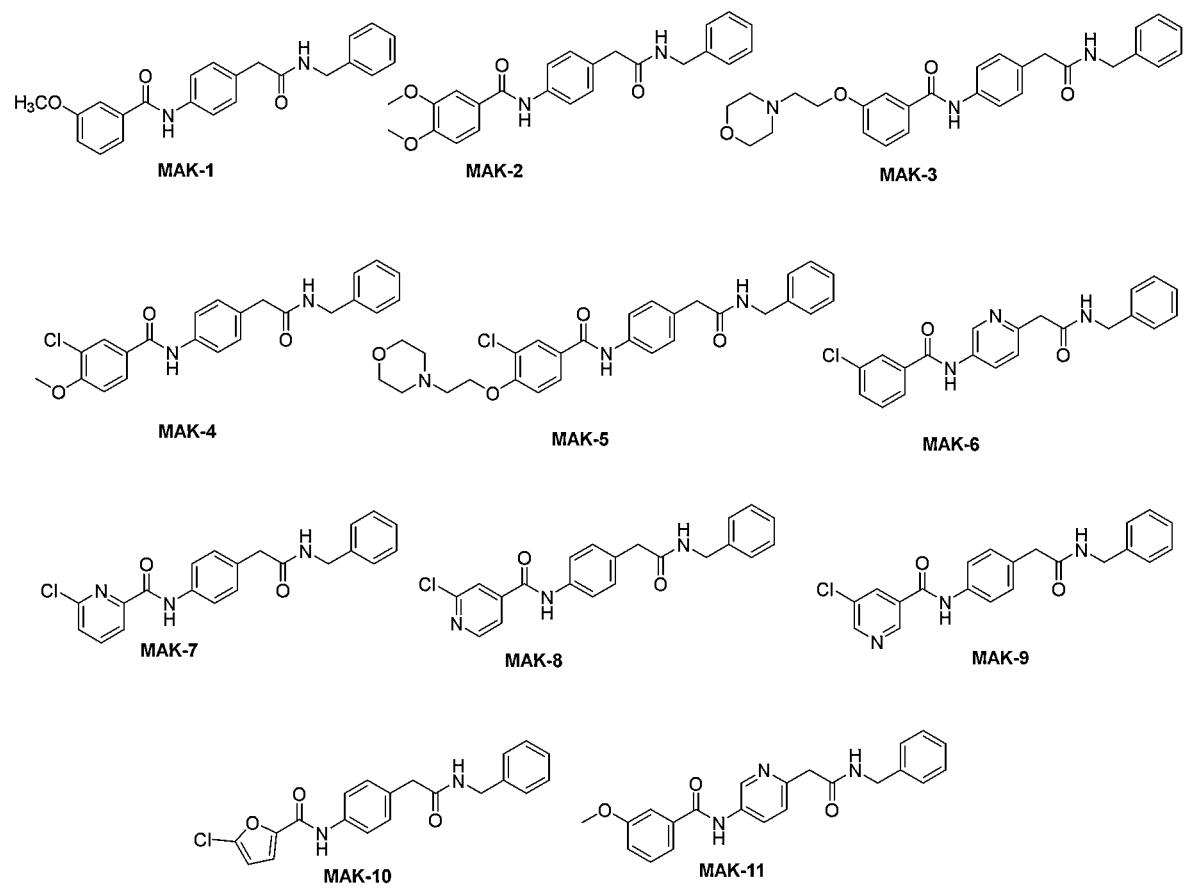
FIG. 3 is a Table of Activities of KAC-12 and its analogues MAK-1 and MAK-6 (depicted in FIG. 2).
FIG. 4 shows exemplary chemical structures according to the invention.

An aspect of the invention provides the compounds shown in FIG. 4. These compounds demonstrated high potency in inhibiting the growth of breast cancer cell lines and potentially beneficial in treating breast and pancreatic cancer.

In some embodiments, the compounds showed potent inhibition of breast cancer growth in tumor sphere models by either killing the tumor aggregates.

In another aspect of the invention, these representative compounds effectively eliminated or reduced the size of tumor spheres at their $IC_{50}$ concentrations.

In addition, the compounds were safe or significantly less toxic on non-cancerous (normal) cell lines.

Furthermore, these compounds inhibited AMPK catalytic activities in high potency.

In addition, these compounds had acceptable drug like profile such as acceptable aqueous solubility and microsomal stability (in presence and in absence of NADPH) and plasma stability.

The compounds of FIG. 4 did not inhibit cytochrome P450 enzymes such as 3A4, 2D6 and 2C9 indicating less possibility of drug-drug interactions.

Moreover, the compounds of FIG. 4 had acceptable ratio of plasma protein binding because the free drug in plasma was in a range sufficient to produce the desired therapeutic activities.

In addition, representative compounds of those shown in FIG. 4 were able to increase mitochondrial membrane depolarization within cancer cell aggregates, which is usually consequent to AMPK decreased activities.

The compounds were able to elevate reactive oxygen species (ROS) and the oxidative stress within breast cancer cell aggregates, which agrees with mitochondrial changes consequent to AMPK inhibition.

AMPK inhibition of the compounds MAK-1 to MAK-11 demonstrate that they are useful for treatment of malignant breast tumors characterized with aberrant increase in basal AMPK signal.

Methodology
Chemical Synthesis

Figure 5:
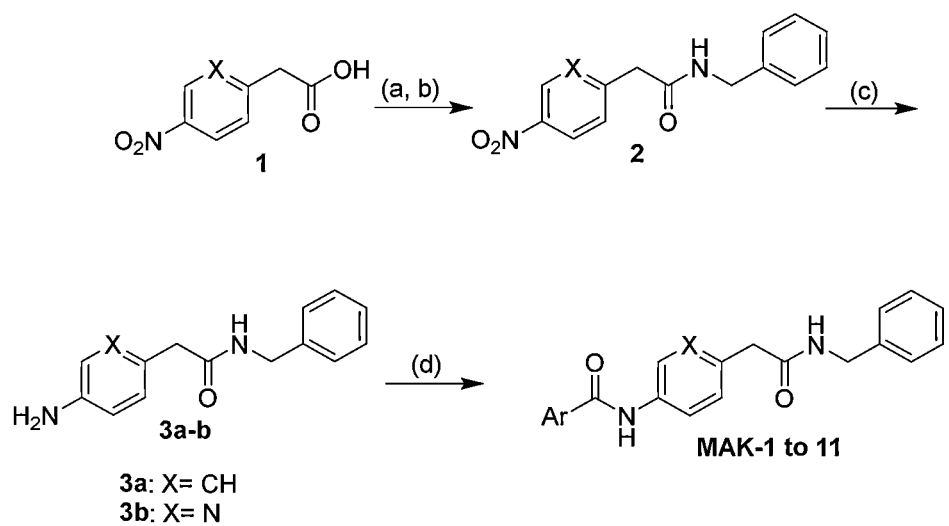
FIG. 5 is a chemical synthesis scheme wherein (a) $(COCl)_2$, DCM, DMF (cat.). (b) $BnzNH_2$, DIPEA, DCM. (c) H-Cube Pro, Pd—C(10%), 10 atm, 40° C., ethyl acetate. (d) $ArCO_2H$, EDC-HCl, HOAt, DMA or ArCOCl, DIPEA, DCM.

The compounds were synthesized to the method illustrated in the scheme shown in FIG. 5. The desired 4-acylamino-N-benzylphenylacetamide derivatives could be accessed from 4-nitrophenylacetic acid 1 in three steps via a straight-forward synthetic strategy. Compound 1 was activated by conversion to the corresponding acid chloride. Without isolation, the acid chlorides were reacted with benzylamine to provide the 2a-b. Reduction of nitro group to afford amines 3a-b was accomplished through hydrogenation. Acylation of 3a-b provided the final products MAK-1 to MAK-11. The synthesis of each is described below.

N-(4-(2-(benzylamino)-2-oxoethyl)phenyl)-3-methoxybenzamide (MAK-1)

3-Methoxybenzoic acid (3.482 g, 2.29 mmol, 1.1 eq.) and 3H-[1,2,3]triazolo[4,5-b]pyridin-3-ol (HOAt) (1.631 g, 2.29 mmol, 1.1 eq.) were added to a solution of 3a (0.5 g, 2.08 mmol, 1 eq.) in dry DMA (3 mL). The resulting mixture was cooled to 0° C., then EDC (3.877 g, 2.5 mmol, 1.2 eq.) was added dropwise. The reaction mixture was stirred at RT overnight. Then 20 mL $H_2O$ was added to reaction mixture and extracted with EtOAc (2×15 mL). All the organic layers were combined, washed with water (3×10 mL), dried over $Na_2SO_4$, and concentrated under vacuum. The resulting material was triturated in i-PrOH/hexane, the solid precipitate was filtrated, washed i-PrOH then hexane, and dried in vacuum to give 0.39 g of MAK-1 (Yield 78%). Melting point 161° C. $^1$H NMR (400 MHz, DMSO-$d_6$) δ 10.19 (s, 1H), 8.52 (t, J=6.0 Hz, 1H), 7.70 (d, J=8.1 Hz, 2H), 7.55 (d, J=7.7 Hz, 1H), 7.50 (d, J=2.6 Hz, 1H), 7.44 (t, J=7.9 Hz, 1H), 7.31 (t, J=7.4 Hz, 2H), 7.24 (q, J=7.7, 6.9 Hz, 5H), 7.15 (dd, J=8.2, 2.6 Hz, 1H), 4.28 (d, J=5.9 Hz, 2H), 3.84 (s, 3H), 3.46 (s, 2H). $^{13}$C NMR (126 MHz, DMSO-$d_6$) δ 170.69, 165.56, 159.66, 139.96, 137.94, 136.83, 132.20, 130.00, 129.60, 128.74, 127.69, 127.23, 120.87, 120.31, 117.74, 113.36, 55.82, 42.71, 42.32. LC-MS (ESI), RT=1.296 min; m/z 375.20 [M+H]$^+$. HRMS (ESI), RT=6.017 min, m/z 375.17065 [M+H]$^+$, formula $C_{23}H_{22}N_2O_3$.

N-(4-(2-(benzylamino)-2-oxoethyl)phenyl)-3,4-dimethoxybenzamide (MAK-2)

The compound was synthesized by reacting 3,4-dimethoxybenzoic acid with 3a following the method used for MAK-1. The reaction yielded 0.325 g (65%) of compound MAK-2. Melting point 215° C. $^1$H NMR (400 MHz, DMSO-$d_6$) δ 10.04 (s, 1H), 8.52 (t, J=6.0 Hz, 1H), 7.68 (d, J=8.1 Hz, 2H), 7.63 (d, J=8.5 Hz, 1H), 7.55 (s, 1H), 7.31 (t, J=7.3 Hz, 2H), 7.24 (d, J=6.8 Hz, 5H), 7.08 (d, J=8.4 Hz, 1H), 4.28 (d, J=5.9 Hz, 2H), 3.85 (s, 3H), 3.84 (s, 3H), 3.46 (s, 2H). $^{13}$C NMR (126 MHz, DMSO-$d_6$) δ 170.71, 165.23, 152.07, 148.78, 139.97, 138.11, 131.95, 129.56, 128.74, 127.69, 127.47, 127.23, 121.46, 120.90, 111.53, 111.37, 56.13, 42.70, 42.32. LC-MS (ESI), RT=1.242 min; m/z 404.20 [M+H]$^+$. HRMS (ESI), RT=5.776 min, m/z 404.17465 [M+H]$^+$, formula $C_{24}H_{25}N_2O_4$.

N-(4-(2-(benzylamino)-2-oxoethyl)phenyl)-3-(2-morpholinoethoxy)benzamide (MAK-3)

$K_2CO_3$ (1.3 g, 9.42 mmol) was added to a solution of methyl 3-hydroxybenzoate (0.573 g, 3.77 mmol) in DMF (7 mL). The resulting mixture was stirred at RT for 15 min, then 4-(2-bromoethyl)morpholine (1.14 g, 4.15 mmol) in form of hydrobromide salt was added to the solution and stirred at 50° C. for 3 h. The reaction mixture was cooled to RT, poured into cold water (50 mL) and extracted with EtOAc (3×30 mL). All the organic layers were combined, washed with water (2×20 mL), dried over $Na_2SO_4$, and concentrated under vacuum. The resulting material was dissolved in THF (10 mL) and then was added aqueous LiOH solution (10%, 2 mL). The resulting mixture was stirred at RT for 16 h. The reaction mixture was evaporated in vacuum to dryness, and the residue was triturated in ether, dried in vacuum and used in next stage as Li salt (0.785 g, 90%).

Then, Li$^+$ salt of 3-(2-morpholinoethoxy)benzoic acid reacted with 3a following the method used for MAK-1. The reaction produced 0.282 g (56.4%) of MAK-3, Melting point 152° C. $^1$H NMR (400 MHz, DMSO-$d_6$) δ 10.17 (s, 1H), 8.52 (t, J=6.1 Hz, 1H), 7.70 (d, J=8.1 Hz, 2H), 7.53 (d, J=9.1 Hz, 2H), 7.43 (t, J=7.9 Hz, 1H), 7.39-7.08 (m, 8H), 4.28 (d, J=5.9 Hz, 2H), 4.16 (t J=5.9 Hz, 2H), 3.59 (s, 4H), 3.46 (s, 2H), 2.73 (t, J=5.7 Hz, 2H), 2.50 (s, 5H). $^{13}$C NMR (126 MHz, DMSO-$d_6$) δ 170.68, 165.48, 158.86, 139.96, 137.93, 136.75, 132.19, 130.02, 129.59, 128.74, 127.69, 127.23, 120.85, 120.43, 118.13, 114.02, 66.68, 66.04, 57.50, 54.13, 42.70, 42.32. LC-MS (ESI), RT=1.060 min; m/z 474.00 [M+H]$^+$. HRMS (ESI), RT=4.733 min, m/z 474.23898 [M+H]$^+$, formula $C_{28}H_{31}N_3O_4$.

N-(4-(2-(benzylamino)-2-oxoethyl)phenyl)-3-chloro-4-methoxybenzamide (MAK-4)

The compound was synthesized using 3-chloro-4-methoxybenzoic acid according to the procedure for the synthesis of MAK-1. The reaction produced 0.375 g (75%) of MAK-4, Melting point 186° C. $^1$H NMR (400 MHz, DMSO-$d_6$) δ 10.15 (s, 1H), 8.52 (t, J=6.1 Hz, 1H), 8.09 (d, J=2.2 Hz, 1H), 7.98 (dd, J=8.7, 2.2 Hz, 1H), 7.68 (d, J=8.1 Hz, 2H), 7.39-6.94 (m, 8H), 4.28 (d, J=5.9 Hz, 2H), 3.94 (s, 3H), 3.46 (s, 2H). $^{13}$C NMR (126 MHz, DMSO-$d_6$) δ 170.68, 163.96, 157.47, 139.96, 137.91, 132.16, 129.62, 128.91, 128.74, 128.18, 127.69, 127.22, 121.34, 120.83, 112.81, 56.95, 42.70, 42.31. LC-MS (ESI), RT=1.354 min; m/z 409.20 [M+H]$^+$. HRMS (ESI), RT=6.265 min, m/z 409.13175 [M+H]$^+$, formula $C_{23}H_{21}ClN_2O_3$.

N-(4-(2-(benzylamino)-2-oxoethyl)phenyl)-3-chloro-4-(2-morpholinoethoxy)benzamide (MAK-5)

The Li salt of 3-chloro-4-(2-morpholinoethoxy)benzoic acid starting material was synthesized following the method used for the synthesis of 3-(2-morpholinoethoxy)benzoic acid Li salt mentioned above within the synthesis of MAK-3, and final product MAK-5 according to the procedure used for the synthesis of MAK-1. The reaction produced 0.323 g (64.6%) of MAK-5, Melting point 147° C. $^1$H NMR (400 MHz, DMSO-$d_6$) δ 10.14 (s, 1H), 8.50 (d, J=6.4 Hz, 1H), 8.08 (s, 1H), 7.96 (d, J=8.7 Hz, 1H), 7.68 (d, J=8.1 Hz, 2H), 7.37-7.28 (m, 3H), 7.24 (d, J=6.9 Hz, 5H), 4.28 (d, J=5.8 Hz, 4H), 3.58 (t, J=4.6 Hz, 4H), 3.46 (s, 2H), 2.76 (d, J=6.0 Hz, 2H), 2.51 (s, 4H). $^{13}$C NMR (126 MHz, DMSO-$d_6$) δ 170.68, 163.94, 156.78, 139.96, 137.91, 132.16, 129.64, 128.77, 128.19, 127.69, 127.22, 121.60, 120.82, 113.73, 67.79, 66.71, 57.13, 54.17, 42.70, 42.31, 40.93. LC-MS (ESI), RT=0.964 min; m/z 508.2 [M+H]$^+$. HRMS (ESI), RT=4.918 min, m/z 508.19974 [M+H]$^+$, formula $C_{28}H_{30}ClN_3O_4$.

N-(6-(2-(benzylamino)-2-oxoethyl)pyridin-3-yl)-3-chlorobenzamide (MAK-6)

The compound was synthesized by reacting 3-chlorobenzoic acid and 3b according to the procedure for the synthesis of MAK-1. The reaction produced 0.407 g of the compound MAK-6 (51.6%), Melting point 183° C. $^1$H NMR (400 MHz, DMSO-$d_6$) δ 10.51 (s, 1H), 8.84 (s, 1H), 8.59 (s, 1H), 8.12 (d, J=8.4 Hz, 1H), 8.04 (s, 1H), 7.94 (d, J=7.8 Hz, 1H), 7.64 (dd, J=36.6, 7.8 Hz, 2H), 7.49-7.04 (m, 6H), 4.31 (s, 2H), 3.68 (s, 2H). $^{13}$C NMR (126 MHz, CDCl$_3$) δ 169.72, 164.76, 152.00, 141.78, 139.91, 136.79, 134.30, 133.75, 132.12, 130.95, 128.72, 128.52, 127.92, 127.70, 127.21, 127.02, 123.95, 44.81, 42.73. LC-MS (ESI), RT=1.247 min; m/z 380.2 [M+H]$^+$. HRMS (ESI), RT=5.72 min, m/z 380.11641 [M+H]$^+$, formula $C_{21}H_{18}ClN_3O_2$.

N-(4-(2-(benzylamino)-2-oxoethyl)phenyl)-6-chloropicolinamide (MAK-7)

The compound was synthesized using 6-chloropyridine-2-carboxylic acid according to the procedure for the synthesis of MAK-1. The reaction produced 0.293 g (58.6%) of MAK-7, Melting point 192° C. $^1$H NMR (400 MHz, DMSO-$d_6$) δ 10.38 (s, 1H), 8.53 (t, J=6.0 Hz, 1H), 8.12 (s, 2H), 7.93-7.70 (m, 3H), 7.27 (dq, J=23.4, 7.7 Hz, 7H), 4.28 (d, J=5.9 Hz, 2H), 3.48 (s, 2H). $^{13}$C NMR (126 MHz, DMSO-$d_6$) δ 170.62, 161.76, 151.45, 149.65, 141.95, 139.94, 136.90, 132.77, 129.67, 128.74, 127.97, 127.69, 127.23, 122.24, 121.04, 42.71, 42.32. LC-MS (ESI), RT=1.360 min; m/z 380.2 [M+H]$^+$. HRMS (ESI), RT=5.732 min, m/z 380.11667 [M+H]$^+$, formula $C_{21}H_{18}ClN_3O_2$.

N-(4-(2-(benzylamino)-2-oxoethyl)phenyl)-2-chloroisonicotinamide (MAK-8)

The compound was synthesized using 2-chloropyridine-4-carboxylic acid according to the procedure for the synthesis of MAK-1. The reaction produced 0.380 g (76%) MAK-8, Melting point 214° C. $^1$H NMR (400 MHz, DMSO-$d_6$) δ 10.54 (s, 1H), 8.62 (d, J=5.1 Hz, 1H), 8.53 (d, J=6.1 Hz, 1H), 8.00 (s, 1H), 7.87 (d, J=5.1 Hz, 1H), 7.69 (d, J=8.1 Hz, 2H), 7.40-7.26 (m, 4H), 7.24 (d, J=7.2 Hz, 3H), 4.28 (d, J=5.9 Hz, 2H), 3.48 (s, 2H). $^{13}$C NMR (126 MHz, CDCl$_3$) δ 170.59, 162.77, 151.31, 151.16, 145.94, 139.93, 132.98, 129.78, 128.74, 127.70, 127.23, 122.73, 121.74, 120.91, 42.71, 42.30; LC-MS (ESI), RT=1.260 min; m/z 380.2 [M+H]$^+$. HRMS (ESI), RT=5.853 min, m/z 380.11660 [M+H]$^+$, formula $C_{21}H_{18}ClN_3O_2$.

N-(4-(2-(benzylamino)-2-oxoethyl)phenyl)-5-chloronicotinamide (MAK-9)

The compound was synthesized using 5-chlornicotinic acid according to the procedure for the synthesis of MAK-1. The reaction produced 0.381 g (62%) of MAK-9, Melting point 231° C. $^1$H NMR (400 MHz, DMSO-$d_6$) δ 10.48 (s, 1H), 9.05 (s, 1H), 8.83 (d, J=2.4 Hz, 1H), 8.53 (t, J=5.9 Hz, 1H), 8.42 (s, 1H), 7.69 (d, J=8.1 Hz, 2H), 7.29 (t, J=7.2 Hz, 4H), 7.24 (d, J=7.3 Hz, 3H), 4.28 (d, J=5.9 Hz, 2H), 3.47 (s, 2H); $^{13}$C NMR (126 MHz, DMSO-$d_6$) δ 170.61, 162.87, 151.01, 147.57, 139.94, 137.42, 135.43, 132.75, 132.27, 131.45, 129.75, 128.74, 127.70, 127.23, 120.80, 42.71, 42.30. LC-MS (ESI), RT=1.252 min; m/z 380.2 [M+H]$^+$. HRMS (ESI), RT=5.821 min, m/z 380.11641 [M+H]$^+$, formula $C_{21}H_{18}ClN_3O_2$.

N-(4-(2-(benzylamino)-2-oxoethyl)phenyl)-5-chlorofuran-2-carboxamide (MAK-10)

The compound was synthesized using 5-chlorofuran-2-carboxylic acid according to the procedure for the synthesis of MAK-1. The reaction produced 0.375 g (75%) of MAK-10, Melting point 217° C. $^1$H NMR (400 MHz, DMSO-$d_6$) δ 10.19 (s, 1H), 8.52 (t, J=6.0 Hz, 1H), 7.64 (d, J=8.1 Hz, 2H), 7.41 (d, J=3.6 Hz, 1H), 7.31 (t, J=7.4 Hz, 2H), 7.28-7.16 (m, 5H), 6.74 (d, J=3.7 Hz, 1H), 4.27 (d, J=5.9 Hz, 2H), 3.46 (s, 2H). $^{13}$C NMR (126 MHz, DMSO-d$_6$) δ 170.63, 155.47, 147.57, 139.94, 138.26, 137.08, 132.48, 129.69, 128.73, 127.69, 127.22, 120.90, 117.34, 109.97, 42.70, 42.28. LC-MS (ESI), RT=1.299 min; m/z 369.2 [M+H]$^+$. HRMS (ESI), RT=6.036 min, m/z 369.10063 [M+H]$^+$, formula $C_{20}H_{17}ClN_2O_3$.

N-(6-(2-(benzylamino)-2-oxoethyl)pyridin-3-yl)-3-methoxybenzamide (MAK-11)

To a solution of 3-methoxybenzoic acid (1 g, 6.6 mmol) in DCM (20 mL) under $N_2$ was added thionyl chloride (1 mL) and 3 drops of DMF. After stirring for 2 h at rt, the solvent was evaporated, and the 3-methoxybenzoyl chloride product was used as is in the next step. A solution of 3-methoxybenzoyl chloride (6.6 mmol) in THF (20 mL) was added slowly to a cooled solution of 3b (7.9 mmol) and triethylamine (20 mmol). The reaction mixture was stirred at 0° C. and left to warm to room temperature. The reaction was left to continue overnight. After evaporating the solvent, the brown residue was reconstituted in EtOAc, in which was insoluble. The solid was filtered and washed with EtOAc till it turned white, followed by $NaHCO_3$, water, brine, and finally with acetone. The solid was recrystallized from acetone to yield (343.5 mg, 13.9%) of the product MAK-11 as white crystalline powder, Melting point 160-161° C. $^1$H NMR (850 MHz, DMSO-d$_6$) δ 11.29 (s, 1H), 9.12 (br t, 1H, J=5.8 Hz), 8.32 (d, 1H, J=4.7 Hz), 8.23 (d, 1H, J=8.0 Hz), 7.60 (d, 1H, J=7.8 Hz), 7.57 (s, 1H), 7.48 (t, 1H, J=7.8 Hz), 7.37 (dd, 1H, J=4.7, 8.0 Hz), 7.3-7.3 (m, 2H), 7.2-7.3 (m, 3H), 7.19 (dd, 1H, J=1.9, 8.2 Hz), 4.32 (d, 2H, J=5.7 Hz), 3.95 (s, 2H), 3.82 (s, 3H); $^{13}$C NMR (214 MHz, DMSO-d$_6$) δ 171.4, 165.3, 159.8, 149.1, 145.4, 139.2, 135.9, 134.3, 131.9, 130.3, 128.8, 127.7, 127.4, 122.9, 120.1, 118.4, 112.9, 55.7, 43.4, 42.9; LCMS: RT=5.4 min; m/z 376.1 [M+H]$^+$.

AMPK Kinase Assay
Preliminary Assay Using R&D Phosphoproteome Array
Cell Culture of HL60 Cell Line HL60, K562, MV4-11 and NB4 were purchased from CLS Cell Line Service GmbH (Eppelheim, Germany). All cell lines were cultured in RPMI-1640 medium supplemented with 10% fetal bovine serum (FBS) (Thermo Fisher Scientific) and 0.1% ciprofloxacin (2.5 mg/ml; Cipla Limited; Mumbai, India), and were maintained at 37° C. in the presence of 21% $O_2$ and 5% $CO_2$.

Cell Viability Assay of HL60 Cell Lines

Cell viability was determined using the CellTiter®-Blue Cell Viability Assay kit (Promega, Madison, Wis., USA). Approximately $10^4$ cells were counted and plated in a 96-well plate in the presence of test compounds ranging from 0.01 to 10 or 20 µM in triplicate and were incubated for 48 h at 37° C. in a humidified incubator. After the incubation period was complete, 20 µL of CellTiter®-Blue Cell Viability Assay reagent was added to each well and incubated for additional 2 h for the development of florescence. Florescence was measured at Ex/Em 540/590 on SpectraMax® i3 Multi-Mode microplate reader (Molecular Devices, LLC; San Jose, Calif., USA) and plotted against drug concentration to determine the $IC_{50}$ of the test compounds. The $IC_{50}$ was obtained by non-linear regression model using GraphPad Prism 6.07 (GraphPad Software, Inc, USA).

Phosphoproteome Array Test

The phosphorylation profile of AMPK kinase (among other 37 kinases) was performed using the Proteome Profiler Human Phospho-Kinase Antibody Array Kit by R&D Systems (Minneapolis, Minn., USA) according to the protocol. Briefly, the total cellular protein was extracted using the Lysis buffer and was quantified using Bio-Rad DC Protein Assay kit (Hercules, Calif., USA). Nitrocellulose membrane set (A&B), pre-spotted with kinase-specific capture antibodies, were first blocked with Array Buffer-1 at RT for 30 min on a rocking platform shaker. Approximately 600 µg of protein concentrate was diluted in the buffer provided and was added onto the membrane set, and the membranes were incubated overnight at 4° C. in an 8-well plate. Subsequently, membranes were washed with Wash Buffer and incubated with appropriate Detection Antibody cocktails for 2 h at RT. Streptavadin-HRP (1:2000) was added onto membranes and incubated for 30 min at RT. Membranes were washed, and Chemiluminescent Detection Reagents 1&2 were applied in equal volumes for detection. The signals were detected on C-DiGit® Blot Scanner (LI-COR, Odyssey Imaging Systems, Lincoln, Nebr., USA) using Image Studio 5.0 software.

Cell-Free AMPK Inhibition Assay

The inhibitory effect of serial concentrations of MAK compounds on AMPK Kinase activity was investigated using the highly sensitive AMPK (A1/B1/G2) Kinase Enzyme assay system (Promega, Madison Wis. USA). This system includes a recombinant full-length human AMPK enzyme and a substrate for the enzyme. The experiment was conducted according to the manufacturer's instructions in the provided protocol. Mean values of replicates were calculated in comparison to the control group.

Evaluation of MAK-1, MAK-6 and MAK-11 in 3-Dimensional (3D) Spheroid Cell Culture Model
Tissue Culture of Breast Cancer Cell Lines
Cell Culture in 3D Model $1 \times 10^4$ cells of each cell line (MCF7 and T47D) were seeded into ultra-low attachment 96 well plate at 37° C. and grown for 48 hours in DMEM media to result in the formation of spheroids. Then, the cells were subjected to the different treatment conditions before performing the assays. The images to demonstrate morphological changes were captured using Nikon (USA) inverted light microscope.

Cytotoxicity Assay in Spheroid Culture Systems

The cytotoxic effects of MAK compounds were assessed against MCF7 and T47D cell lines using MTT cell viability assay. The cells were treated for 48 hours with different concentrations of each MAK compound and the control cells were subjected to the vehicle (0.1% DMSO). Then, 10% of 5 mg/mL MTT was added to each well containing treated or control cells, and mixture was incubated at 37° C. for 3 hours. After that, the MTT-containing media was replaced with 100 µL DMSO and incubated for 10 minutes at room temperature before measuring the absorbance for each well at 570 nm. According to the measured absorbance, the $IC_{50}$ was calculated for each compound. All the experiments were performed in biological and experimental replicates.

Mitochondrial Membrane Potential Assay

The mitochondrial membrane potential was investigated in response to the treatment with MAK compounds. This assay depends on the measurement of the aggregate fluorescence for Tetraethylbenzimidazolylcarbocyanine iodide (JC-1). This cationic dye accumulates in the energized mitochondria, and the increase in aggregate fluorescence indicates mitochondrial hyper-polymerization while the reduction indicates the depolarization state.

After growing the cells and treating them with MAK compound for 48 hours, 2 µM of JC-1 final concentration was added and the mixture was incubated for 1 hour at 37°

C. in presence of 5% $CO_2$. Then, the samples were analyzed using flow cytometry. Mean values and standard deviation of replicates were calculated in comparison to the control group.

Live and Dead Assay of Tumor Spheroids

The Live/Dead assay contains a mixture of two staining fluorescent dyes that label live and dead cells to enable differentiation between them. The cell viability of the cells in response to the treatment with MAK compounds was examined. The cells were grown for 48 hours and treated with MAK compound for additional 48 hours, then Cytox RED solution reagent was added. After incubation at 37° C. under 5% $CO_2$ for 1 hour, the samples were immediately analyzed by flow cytometry. Mean values and standard deviation of replicates were calculated in comparison to the control group.

Reactive Oxygen Species (ROS) Assay

The CELLROX (Invitrogen) assay was used to measure the level of reactive oxygen species (ROS) in live cells. This cell permeable reagent functions as a fluorogenic probe that exhibits weak fluorescence in the reduced environment and produces photo-stable fluorescence when oxidized by ROS. The technique was used to investigate the capability of tested compounds to induce intracellular ROS. After forming the spheroids for 48 hours and treating them for additional 48 hours with MAK compound, spheroids were incubated in culture medium with 500 nM CellROX for 60 minutes at 37° C. in presence of 5% $CO_2$, and the samples were immediately analyzed on flow cytometry using 488-nm excitation for the CellROX® Green.

Evaluation of MAK-1 to MAK-11 for Inhibition of Breast Cancer Cell Lines in Monolayer Cell Culture Model Cell Culture in Monolayer $1 \times 10^6$ cells of the human breast cancer cell lines MCF7 and T47D were seeded and grown at 37° C. with 5% $CO_2$, in a Dulbecco's Modified Eagle Medium (DMEM) with 10% fetal bovine serum (Sigma). The cells were maintained until they reached the confluence over 90%. Then, the cells were subjected to the different treatment conditions before performing the assays.

Cytotoxic Assay in Monolayer Model

The cytotoxic effects of MAK compounds were assessed against MCF7 and T47D cell lines using MTT cell viability assay. The cells were treated for 48 hours with different concentrations of each MAK compound and the control cells were subjected to the vehicle (0.1% DMSO). Then, 10% of 5 mg/mL MTT was added to each well containing treated or control cells, and mixture was incubated at 37° C. for 3 hours. After that, the MTT-containing media was replaced with 100 µL DMSO and incubated for 10 minutes at room temperature before measuring the absorbance for each well at 570 nm. According to the measured absorbance, the $IC_{50}$ was calculated for each compound. All the experiments were performed in biological and experimental replicates.

Druggability Evaluation of MAK-1 and MAK-6

There is a universal agreement that the physicochemical and pharmacokinetic properties play an important role in the viability of compounds as leads that can be optimized into drug candidates. Early in vitro screening of compounds in high throughput assays that predict in vivo ADME properties has become the norm for drug discovery, both in the industrial and academic setting. Properties such as aqueous solubility and protein binding impact not only in vivo studies but also biochemical and in vitro cellular assays as well. Cancer cells are well known to express elevated levels of hydrolytic enzymes as well, so assessment of the potential liability to hydrolytic metabolism is another important consideration for anti-cancer hits and leads especially that our compounds contain two amidic functionalities.

Maximum Kinetic Aqueous Solubility

Solubility assays were performed using Millipore Multi-Screen® HTS-PFC Filter Plates designed for solubility assays (EMD Millipore, Billerica, Mass.). Assays were run in triplicate. The 96-well plates consist of two chambers separated by a filter. Liquid handling was performed using JANUS® Verispan and MTD workstations (Perkin Elmer, Waltham, Mass.). 4 µL of MAK-1 or MAK-6 solution (10 mM in DMSO) was added to 196 µL of phosphate buffer (45 mM potassium phosphate, 45 mM sodium acetate, 45 mM ethanolamine, pH=7.4) in the top chamber to give a final DMSO concentration of 2% and a theoretical drug concentration of 200 µM. Plates were gently shaken for 90 min and then subjected to vacuum. Insoluble drug is captured on the filter. 160 µL of the filtrate is transferred to 96-well Griener UV Star® analysis plates (Sigma-Aldrich, St. Louis, Mo.) containing 40 µL of acetonitrile. The test compound concentration in the filtrate is measured by UV absorbance on a Spectromax® Plus microplate reader (Molecular Devices, Sunnyvale, Calif.) using Softmax Pro software v.5.4.5. Absorbances at 5 wavelengths (280, 300, 320, 340, and 360 nm) were summed to generate the UV signal. Standard curves were generated by adding 4 µL of five concentrations of test compound in DMSO to 40 µL of acetonitrile in UV Star plates followed by 156 µL of the appropriate solubility medium. Analysis and statistics were performed using GraphPad® Prism v.5.04. Data were reported as the maximum concentration observed in the filtrate.

Stability in Mouse and Human Liver Microsomes

The clearance of MAK-1 and MAK-6 in mouse or human liver microsomes was determined at 37° C. as previously described (Yang et al., 2007). Both mouse and human liver microsomes were obtained from Merck KGaA, (Darmstadt, Germany), Cat. No. M9441 (Mouse liver microsomes) and M0317 (Human liver microsomes). Assays were conducted in triplicate in 96-deep well polypropylene plates. The compounds were incubated with pooled liver microsomes from male CD-1 mice (Life Technologies, Grand Island, N.Y.), tetra-sodium NADPH and magnesium chloride for 60 min at 37° C. with gentle shaking. At five time points, reaction mixture aliquots were transferred to 96-shallow well stop plates on ice containing acetonitrile with 0.1 µM propafenone. Control reactions (lacking NADPH) were performed in a similar manner to demonstrate NADPH dependency of compound loss and assess the potential for hydrolysis of compounds in liver tissue. Standard curves for test compound were generated using 5 concentrations in triplicate that were processed as above but with zero incubation time. Stop plates were centrifuged at 2000 g for 10 min and then supernatant aliquots were transferred to a Waters Aquity® UPLC 700 µL 96-well sample plate with cap mat (Waters, Milford, Mass.). The amount of compound remaining in the supernatant was quantified by LC/MS/MS using a Waters Xevo TQ MS (electrospray positive mode) coupled to a Waters Aquity® UPLC (BEH column, C18). Propafenone was used as the internal standard. GraphPad® Prism v 5.04 was used for nonlinear fitting of time course data to generate $t_{1/2}$ values.

Inhibition Assay of Human CYP450 Enzymes

The two compounds MAK-1 and MAK-6 were assessed for its ability to inhibit the three major human CYP450 enzymes, 3A4, 2D6 and 2C9. Assays were run in triplicate. Expressed enzymes in insect supersomes (Fisher Scientific, Waltham, Mass.) were used to minimize non-specific binding and membrane partitioning issues (McMasters et al., 2007). The 3A4 assay uses testosterone as a substrate and analysis was performed by LC/MS/MS on a Waters Xevo TQ instrument as described above using positive electrospray ionization. Assay acceptance criteria was 20% for all standards and 25% for the LLOQ. The 2D6 and 2C$_9$ assays use fluorescent substrates (3-[2-(N,N-diethylamino)ethyl]-7-methoxy-4-methylcoumarin for 2D6; 7-methoxy-4-(trifluoromethyl)coumarin for 2C$_9$) and were analyzed on an Envision plate reader. GraphPad® Prism v 5.04 was used for nonlinear fitting of data to generate IC$_{50}$ values.

Stability in Mouse Plasma

The assay is conducted at 37° C. in triplicate. Test compounds or procaine (positive control) are tested at a final concentration of 1 µM in either 2.5% DMSO/CD-1 mouse plasma (Innovative Research, Novi, Mich.; sodium heparin added as anticoagulant; pH adjusted to 7.4 with 2N HCl on day of use) or 2.5% DMSO/PBS (pH 7.4: 136.9 mM NaCl, 2.68 mM KCl, 8.1 mM Na$_2$HPO$_4$, 1.47 mM KH$_2$PO$_4$, 0.9 mM CaCl$_2$, 0.49 mM MgCl$_2$). At seven time points, reaction mixture aliquots were transferred to 96-shallow well stop plates on ice containing acetonitrile with 0.1 µM propafenone. Samples were analyzed by LC/MS/MS on a Waters Xevo TQ instrument as described above using positive electrospray ionization. Assay acceptance criteria was 20% for all standards and 25% for the LLOQ. GraphPad® Prism v. 5.04 was used for nonlinear fitting of data to generate t$_{1/2}$ values.

Binding to Mouse Plasma Proteins

The equilibrium dialysis method for determining plasma protein binding was performed as previously described using 96-well dialyzer plates with molecular weight cutoff of 5K (Harvard Apparatus, Holliston, Mass.) and a dual-plate rotator set to maximum speed (Harvard Apparatus, Holliston, Mass.) located in a 37° C. incubator with a 10% CO$_2$-atmospheric environment. Assays were run in triplicate. The test compounds were added to CD-1 mouse plasma (Innovative Research, Novi, Mich., sodium heparin added as anticoagulant; pH adjusted to 7.4 with 2N HCl on day of use) in DMSO (final DMSO concentration 0.4%) to give 10 µM final concentration. Drug/plasma mixture and buffer (Dulbecco's phosphate-buffered saline 1× without calcium and magnesium, Mediatech, Inc., Herndon, Va.) were placed in their respective sides, wells were capped, and the plate was placed in the rotator and allowed to dialyze for 22 h. Following dialysis, aliquots of buffer and plasma mixture were removed and mixed with aliquots of the opposite matrix in 96-well deep plates. Concentrations of analytes from each side of the dialysis plate were determined by LC/MS/MS on a Waters Xevo TQ instrument as described above using positive electrospray ionization. Assay acceptance criteria was 20% for all standards and 25% for the LLOQ. The fraction unbound was calculated by dividing the drug concentration in the buffer side of the dialysis plate by the drug concentration in the plasma side.

Safety of the Compounds on Non-Cancerous (Normal) Cell Lines.

In addition to have a good physicochemical profile, it is important for a studied lead to differentiate between cancer cells and highly proliferating non-cancerous cells. Therefore, we assessed compounds MAK-1 and MAK-6 for both the in silico and in vitro physicochemical characteristics as well as for cytotoxic effect on human skin fibroblasts (SKF) cell lines. Cytotoxicity was determined using Sulforhodamine B (SRB) method. Exponentially growing human skin fibroblast cells (Nawah Scientific, Cairo, Egypt) were collected using 0.25% Trypsin-EDTA and were then seeded in 96-well plates at a density of 1000-2000 cells/well in 10% FBS and penicillin/streptomycin supplemented RPMI-1640 medium. After 24 h, cells were treated with different concentrations of test compounds and incubated for 72 h at 37° C. in a humidified atmosphere containing 5% CO$_2$. Next, the cells were fixed by adding trichloroacetic acid (TCA, 10% final conc. in wells) directly to the wells and incubated for 1 h at 4° C., then cells were washed with distilled water 5 times to remove excess TCA, media, serum proteins, and metabolites, followed by air drying. After that, the fixed cells were stained with 0.4% SRB dissolved in 1% acetic acid for 10 min at room temperature, and excess stain was removed by quickly rinsing with 1% acetic acid. The residual acetic acid was removed completely by air drying the plates for 24 h, and the dye was solubilized with Tris buffer (pH=7.4, 10 mM) for 5 min on a shaker at 1600 rpm. The optical density (OD) of each well was measured spectrophotometrically at 564 nm with an ELISA microplate reader (ChroMate-4300, FL, USA). The IC$_{50}$ values were calculated according to the equation for Boltzman sigmoidal concentration—response curve using the nonlinear regression fitting models (Graph Pad, Prism Version 5).

Results

Biological Screening Results

MAK-1, MAK-6 and MAK-11 Inhibited AMPK Kinase Activity

Based on our previous results, we then assessed the impact of MAK-1, MAK-6 and MAK-11 on the kinase activity of AMPK enzyme. We used escalating concentrations from each of the studied compounds to measure the kinase activity of AMPK using recombinant protein system. As illustrated in FIG. 6, MAK-1, MAK-6 and MAK-11 have shown potent inhibitory effects on the AMPK kinase activity at low nanomolar concentrations. The IC$_{50}$ of the AMPK enzyme activity for MAK-1, MAK-6 and MAK-11 were 4.8 nM, 5.6 nM and 5.8 nM, respectively. From the observed results, the novel compounds could be classified as inhibitors of AMPK kinase activity (see FIGS. 6A, 6B, and 6C).

MAK-1, MAK-6 and MAK-11 Inhibited the Growth Breast Cancer Spheroids

Since 3D cell culture systems provide a more realistic simulation to reflect the tumor microenvironment due to the expression pattern of specific genes, particular cellular behaviors, and cell-cell interactions and crosstalk that cannot be reproduced in monolayer cell cultures [32-34]. Therefore, we evaluated the antiproliferative effects of an initial set of compounds MAK-1, MAK-6 and MAK-11 in spheroids (3D cell culture model) of MCF7 and T47D. Results (see FIG. 7) illustrates that the IC$_{50}$ for MAK-1, MAK-6 and MAK-11 (23.81±0.16)µM, (22.87±0.245)µM, and (19.58±0.525)µM respectively for MCF7 and for T47D IC$_{50}$ for compounds were (13.9±0.095)µM, (7.29±0.085)µM, and (3.72±0.03)µM respectively. Similar to monolayer cells, the spheroids showed higher sensitivity in T47D compared to MCF7 in all compounds. Ultimately, T47D is more sensitive to our compounds' treatment compared to MCF7; furthermore, increased levels of IC$_{50}$ in spheroids could be due to spheroids associated cancer stemness. The IC$_{50}$ of MAK-1, MAK-6 and MAK-11 were used for spheroid treatment at 48 h. Interestingly, all formed spheroids showed noticeable reduction post treatment with MAK-1, MAK-6 and MAK-11 as illustrated in the images of FIG. 8. Effective reductions of spheroid aggregates were observed in all treatments compared to control (vehicle; 0.1% DMSO). Overall, our results showed significant (p<0.05) anti-proliferative effect against both monolayer and spheroid breast cancer models (see FIG. 7).

Mitochondrial Depolarization Assay in Spheroid Model

Since the novel compounds showed significant anti-proliferative effect against spheroid model, we then performed mitochondrial depolarization assay in spheroids treated with MAK-1, MAK-6 and MAK-11 to determine the effect of the compounds on mitochondrial membrane potential ($\Delta\psi m$). The formed spheroids of both MCF7 and T47D were treated with either MAK-1, MAK-6 and MAK-11 or 0.1% DMSO (as vehicle control). Interestingly, all compounds showed significant ($p<0.05$) elevated depolarization state in mitochondrial membrane in both cell lines as evident by JC-1 dye oxidation (FIG. 9A).

Increased depolarization state of mitochondrial illustrates defect in mitochondrial function and hence could implicate in apoptosis of cells. The $\Delta\psi m$ depolarization state was found to be increased in MCF7 and T47D spheroids 48 h post treatment with MAK-1, MAK-6 and MAK-11. In MCF7, MAK-11 (34.00±0.87%) has the highest depolarized cells followed by MAK-6 (28.73±0.82%) and then MAK-1 (24.77±0.65%) compared to control (18.01±0.58%). Whereas in T47D, MAK-11 (36.77±0.65%) has the highest depolarized cells followed by MAK-1 (36.77±1.17%) and then MAK-6 (32.77±0.54%) compared to control (15.67±2.05%). From our results MAK-11 showed the highest impact on $\Delta\psi m$. Overall, our results have shown that treatment of spheroids with MAK-1, MAK-6 and MAK-11 promote significant reduction in the mitochondrial membrane polarization state (100-depolarized area) in both cell lines. The decrease in polarization and increase in depolarization states of $\Delta\psi m$ are characteristics features of mitochondrial mediated apoptosis process and cell dead (FIG. 9B).

Live and Dead Assay in Spheroids

To determine the impact of the novel compounds in spheroid cell dead, we performed live and dead assay. The spheroids of both MCF7 and T47D were treated with either MAK-1, MAK-6, MAK-11 or 0.1% DMSO (vehicle control). As shown in FIG. 10A, the number of dead cells were found to be increased in both MCF7 and T47D spheroids treated with the novel compounds compared to the vehicle treated control. Results from live and dead assay showed significant increase in dead cells 48 h post treatment of spheroids with novel compounds (FIG. 10B). In MCF7, highest dead rate was recorded in MAK-11 ((36.48±0.39%), followed by MAK-1 (36.33±0.88%) and then MAK-6 (34.27±0.49%) compared to control (10.33±2.40%). Whereas in T47D, highest dead rate was seen in MAK-1 (42.43±0.49%), followed by MAK-6 (37.97±0.27%) and then MAK-11 (32.10±0.56%) compared to control (2.60±0.31%). Treatment of spheroids with the novel compounds hence, implicates in cell dead with the highest dead event recorded in T47D spheroids.

ROS Levels Modification in Spheroids

To investigate whether cell dead observed post treatment with the novel compounds are associated with reactive oxygen species (ROS), we performed ROS assay using CellROX Green cell permeable dye that is oxidized in presence of free radicals to produce green fluorescence. We observed that all the tested compounds (MAK-1, MAK-6 and MAK-11) have induced intracellular ROS levels in both MCF7 and T47D cell lines. In MCF7, highest ROS level is seen MAK-11 with 25% followed by MAK-1 at 10% and then MAK-6 at 6% in treatment vs control, whereas in T47D highest ROS level was recorded in MAK-11 with 30% followed by MAK-6 at 6% and then MAK-1 at 4%. From the results; MAK-11 has the highest level of induced ROS in both breast cancer cell spheroids. Overall, breast cancer spheroids treatment with the novel compounds showed, significant induction of intracellular ROS levels in both MCF7 and T47D cell lines (see FIG. 11).

MAK Compounds Inhibited MCF7 and T47D Breast Cancer Cell Line Proliferation

Based on the above promising results on challenging tumor spheroid cancer models, we tested a larger set of compounds (MAK-1 to MAK-11) for their growth inhibition activity against human breast cancer cell lines MCF7 and T47D grown in a simple monolayer (adherent, 2-dimensional) cell culture model.

Anti-proliferation activities shown in FIG. 12 indicated that most of the compounds exhibited high growth inhibition activities against both types of breast cancer cell lines, albeit slightly higher sensitivity shown by T47D cells to some of our compounds. In MCF-7 cell line inhibition assay, MAK-2 demonstrated the highest potency in this assay with $IC_{50}=6$ nM. Other notable potencies were observed for MAK-11, MAK-10 and MAK-4 with $IC_{50}$ values=148 nM, 225 nM and 225 nM, respectively.

MAK compounds also showed a range of potencies in the cytotoxic assay against T47D cell lines. MAK-3 and MAK-6 were powerful inhibitors of the MCF7 cells at $IC_{50}=1$ and 1.2 nM, respectively. MAK-11 also showed good potency in this test at 97 nM. Other compounds ranged from few hundred nM to 1 μM level of $IC_{50}$.

Solubility, Microsomal Stability, and Plasma Protein Binding

To address our concerns we tested compounds MAK-1 and MAK-6 in a battery of in vitro ADME assays, which included maximum kinetic aqueous solubility in 2% DMSO/phosphate-buffered saline (PBS), stability in mouse and human liver microsomes in the presence and absence of nicotinamide adenine di-nucleotide phosphate (NADPH), inhibitory activity against the three major human cytochrome P450 metabolizing enzymes (CYP3A4, CYP2D6 and CYP2C9), stability in mouse plasma at 37° C. and plasma protein binding (expressed as percent bound to mouse plasma protein at 37° C.). The results are summarized in FIG. 13.

Compounds MAK-1 and MAK-6 displayed good to moderate solubility in 2% DMSO/PBS because saturation occurred at 9.4 μM and 3.7 μM for MAK-1 and MAK-6, respectively. Compound MAK-1 was moderately stable to oxidative metabolism by mouse and human liver microsomes (35 min) in the presence of NADPH. There was a non-significant loss of compound MAK-1 in mouse liver microsomes lacking NADPH, a trend that was not repeated in human liver microsomes lacking NADPH. Compound MAK-1 was also stable in mouse plasma at 37° C. for the duration of the assay (5 h). These data suggest that MAK-1 is stable to enzymatic hydrolysis in liver and cardiovascular tissue. Compound MAK-1 displayed moderate binding to mouse plasma proteins, with 8.3% free, unbound fraction detected. It showed no inhibition of the three major metabolizing CYP450 enzymes at concentrations up to 10 μM.

The compound MAK-6 was less soluble than MAK-1 in 2% DMSO/PBS (maximum solubility=3.7 μM). The compound was highly stable in presence of human liver microsomes in presence and in absence of NADPH, indicating its low sensitivity to oxidative and non-oxidative metabolic conversions. Compound MAK-6 also did not display any inhibitory activity against metabolizing CYP450 enzymes and its plasma protein biding was as good as that of MAK-1 (8.7% unbound drug).

Normal Cell Line Assay of MAK-1, MAK-6 and MAK-11

The three compounds were evaluated for their effect on the growth and proliferation human skin fibroblasts (HSF) as an example of non-cancerous cell lines. This test determines how a certain compound can differentiate between cancer cells and normal cells. Results Compound MAK-6 and MAK-11 were highly safe to normal cells but very toxic to cancer cells. MAK-1 was less selective but it is still potentially safe because the normal cells were inhibited at 7-fold higher concentrations than MCF7 breast cancer cells (FIG. 14).

Figure 1:
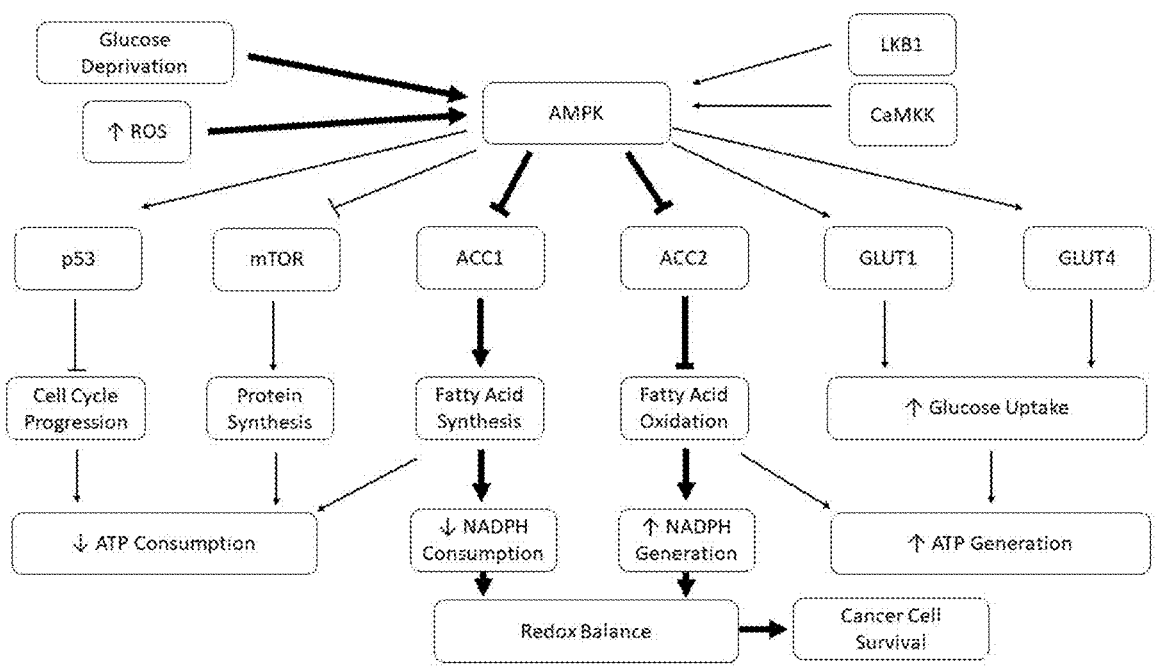
FIG. 1 is a schematic showing the role of AMPK in regulating redox potential to enhance cancer cell survival. Bold arrows highlight ACC1 and ACC2 pathways which AMPK is involved to increase cancer cell survival.
Figure 2:
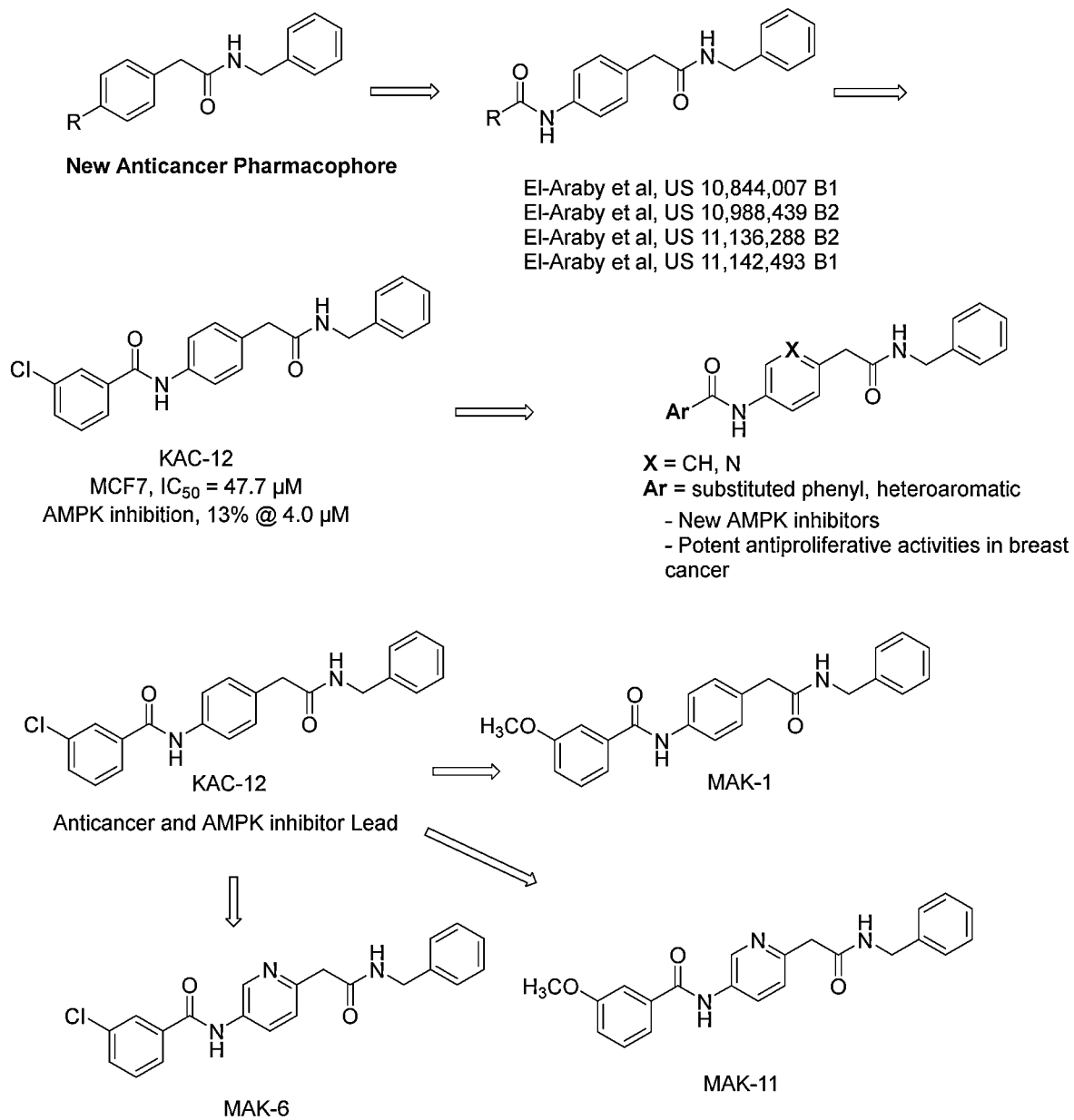
FIG. 2 is a chart showing Step-wise discovery plan for new anticancer compounds by boosting AMPK inhibition of 4-(acylamino)aryl-N-benzylacetamide scaffold.

Aspects of this invention were identified based on the significance of the AMPK target which remained less explored in research as detailed above. The design was based on previously disclosed compound KAC-12 (FIG. 1) which was noticed that it slightly downregulated the activated AMPKα1 signal (phosphoprotein) by 15%. Although the effect of KAC-12, a compound belonging to 4-(acylamino)phenyl-N-benzylacetamide scaffold, was not strong but it met our high interest in the target. Therefore, we designed derivatives to increase activities against AMPK and therefore, bring higher therapeutic benefits against breast cancer. In a preliminary screening, MAK-1 and MAK-6 showed moderate activities against leukemia cell lines HL60 with $IC_{50}$ values at 3.27±0.15 µM and 6.24±3.3, respectively. Using lysates of treated HL-60 cells, the effect on MAK-1 and MAK-6 were tested for their inhibition of AMPK-α2 signal at concentrations of 6 µM and 8 µM, respectively. This test was performed by detecting the intensity of antibody to the phospho-antigen. Surprisingly, both compounds profoundly caused a profound decrease of phospho-protein AMPK-α2 existence by 61.8% and 92.1% for MAK-1 and MAK-6, respectively. In as much as the result was exciting to us, but could not be correlated to a contribution the anticancer activities against the leukemic cell lines because the AMPK is not significantly overexpressed in this cell line and therefore, it does not depend on this factor in their proliferation.

We turned our attention to breast cancer cell lines because they are strongly implicated in the growth of this type of tumors. Using cell-free assays on recombinant proteins, the results were exciting in as much as surprising to us. All three tested compounds (MAK-1, MAK-6 and MAK-11) strongly inhibited AMPK activities at $IC_{50=4.8}$ nM, 5.6 nM and 5.8 nM, respectively. Embarking on a novel target interference, we turned our investigations into breast cancer cell lines MCF7 and T47D. Classically, researchers depended on monolayer (2D) cytotoxic assays, which are still valid approach. However, investigations involving the tumor spheres, though tedious and more expensive, constitute a more realistic evaluation of anticancer compounds. We found that the compounds are very effective in killing tumor spheres (Live-Dead assay) in a dose dependent fashion. The two cell lines did not show similar sensitivity to the compounds, with T47D tumor spheres appear more responsive to the compounds. The compound MAK-11 has the most potent activities against tumor spheres, especially against T47D cells making a strong candidate for development as anticancer therapy especially for treatment of breast cancer based on it AMPK inhibition. The effect on the compounds on grown tumor spheres were illustrated (FIG. 6) as they clearly demonstrated significant size reduction and sometimes, complete disintegration of the tumor aggregates. AMPK kinase pays a role in regulating mitochondrial membrane polarization. AMPK inhibition, therefore, is expected to cause membrane depolarization as cell stress is heightened and cell near apoptotic phase entry. Evident, the three compounds, at their $IC_{50}$ (spheroids) caused highly significant mitochondrial membrane depolarization as indicator of link between cancer cell deaths and AMPK inhibition. Again, MAK-11 showed the highest impact on the mitochondrial membranes. It also showed the highest increase in ROS level elevation to provide more evidence of great effect on AMPK inhibition on these tumor aggregates.

To broaden the investigation, we explored more compounds related to the same pharmacophore of MAK-1, MAK-6 and MAK-11. The large number of compounds necessitated to test on 2d (monolayer) cell lines. Interestingly MAK-6 showed the highest cytotoxic activities against T47D cell line over MAK-1 and MAK-11. This might be attributed to either that the activities on tumor spheres (3D) is more realistic because it has better similarity to tumors.

The eleven compounds differed significantly in their cytotoxic potencies, although all of them demonstrated $IC_{50}$ values less than 1.3 µM. The 3,4-dimethoxy derivative MAK-2 showed highest activity against MCF7 (6 nM) while MAK-3 (3-(2-morpholinoethoxy)phenyl) had the highest activities against T47D at $IC_{50}$=1 nM. The results again suggest that these derivatives are strong candidates for development as anticancer agents.

ACKNOWLEDGEMENT OF SPONSORED RESEARCH

This invention was funded by Institutional Fund Projects under grant number (IFPRC-099-166-2020). Therefore, inventors acknowledge technical and financial support from the Ministry of Education and King Abdulaziz University, Jeddah, Saudi Arabia.

REFERENCES

1. Sarkar, S., et al., *Cancer Development, Progression, and Therapy: An Epigenetic Overview*. International Journal of Molecular Sciences, 2013. 14(10): p. 21087-21113.
2. Sung, H., et al., *Global Cancer Statistics 2020: GLOBOCAN Estimates of Incidence and Mortality Worldwide for 36 Cancers in 185 Countries*. CA Cancer J Clin, 2021. 71(3): p. 209-249.
3. Li, W. D., et al., *Targeting AMPK for cancer prevention and treatment*. Oncotarget, 2015. 6(10): p. 7365-7378.
4. Lin, S. C. and D. G. Hardie, AMPK. *Sensing Glucose as well as Cellular Energy Status*. Cell Metabolism, 2018. 27(2): p. 299-313.
5. Hardie, D. G. and D. R. Alessi, *LKB1 and AMPK and the cancer-metabolism link—ten years after*. BMC Biol, 2013. 11: p. 36.
6. Hadad, S. M., S. Fleming, and A. M. Thompson, *Targeting AMPK. A new therapeutic opportunity in breast cancer*. Critical Reviews in Oncology Hematology, 2008. 67(1): p. 1-7.
7. El-Masry, O. S., B. L. Brown, and P. R. M. Dobson, *Effects of activation of AMPK on human breast cancer cell lines with different genetic backgrounds*. Oncology Letters, 2012. 3(1): p. 224-228.
8. Saraei, P., et al., *The beneficial effects of metformin on cancer prevention and therapy: a comprehensive review of recent advances*. Cancer Management and Research, 2019. 11: p. 3295-3313.
9. Steinberg, G. R. and D. Carling, *AMP-activated protein kinase: the current landscape for drug development*. Nat Rev Drug Discov, 2019. 18(7): p. 527-551.

10. Faubert, B., et al., *The AMP-activated protein kinase (AMPK) and cancer: many faces of a metabolic regulator.* Cancer Lett, 2015. 356(2 Pt A): p. 165-70.
11. Dite, T. A., et al., *AMP-activated protein kinase selectively inhibited by the type II inhibitor SBI-0206965.* Journal of Biological Chemistry, 2018. 293(23): p. 8874-8885.
12. Handa, N., et al., *Structural basis for compound C inhibition of the human AMP-activated protein kinase α2 subunit kinase domain.* Acta Crystallogr D Biol Crystallogr, 2011. 67 (Pt 5): p. 480-7.
13. Yan, Y., et al., *Structure of an AMPK complex in an inactive, ATP-bound state.* Science, 2021. 373(6553): p. 413-419.
14. Jang, T., et al., *5'-AMP-activated protein kinase activity is elevated early during primary brain tumor development in the rat.* Int J Cancer, 2011. 128(9): p. 2230-9.
15. Laderoute, K. R., et al., *5'-AMP-activated protein kinase (AMPK) is induced by low-oxygen and glucose deprivation conditions found in solid-tumor microenvironments.* Mol Cell Biol, 2006. 26(14): p. 5336-47.
16. Ng, T. L., et al., *The AMPK stress response pathway mediates anoikis resistance through inhibition of mTOR and suppression of protein synthesis.* Cell Death Differ, 2012. 19(3): p. 501-10.
17. Vara-Ciruelos, D., M. Dandapani, and D. G. Hardie, *AMP-Activated Protein Kinase: Friend or Foe in Cancer?* Annual Review of Cancer Biology, Vol 4, 2020. 4: p. 1-16.
18. Vara-Ciruelos, D., F. M. Russell, and D. G. Hardie, *The strange case of AMPK and cancer: Dr Jekyll or Mr Hyde? (dagger).* Open Biol, 2019. 9(7): p. 190099.
19. Hu, M. Y., et al., *AMPK Inhibition Suppresses the Malignant Phenotype of Pancreatic Cancer Cells in Part by Attenuating Aerobic Glycolysis.* Journal of Cancer, 2019. 10(8): p. 1870-1878.
20. Hampsch, R. A., et al., *AMPK Activation by Metformin Promotes Survival of Dormant ER(+) Breast Cancer Cells.* Clin Cancer Res, 2020. 26(14): p. 3707-3719.
21. Zadra, G., J. L. Batista, and M. Loda, *Dissecting the Dual Role of AMPK in Cancer: From Experimental to Human Studies.* Mol Cancer Res, 2015. 13(7): p. 1059-72.
22. Jeon, S. M., N. S. Chandel, and N. Hay, *AMPK regulates NADPH homeostasis to promote tumour cell survival during energy stress.* Nature, 2012. 485(7400): p. 661-+.
23. Park, H. U., et al., *AMP-activated protein kinase promotes human prostate cancer cell growth and survival.* Mol Cancer Ther, 2009. 8(4): p. 733-41.
24. Laderoute, K. R., et al., *5'-AMP-activated protein kinase (AMPK) supports the growth of aggressive experimental human breast cancer tumors.* J Biol Chem, 2014. 289(33): p. 22850-22864.
25. Dasgupta, B. and W. Seibel, *Compound C/Dorsomorphin: Its Use and Misuse as an AMPK Inhibitor.* Methods Mol Biol, 2018. 1732: p. 195-202.
26. Deeks, E. D. and G. M. Keating, *Sunitinib.* Drugs, 2006. 66(17): p. 2255-66; discussion 2267-8.
27. Laderoute, K. R., et al., *SU11248 (sunitinib) directly inhibits the activity of mammalian 5'-AMP-activated protein kinase (AMPK).* Cancer Biol Ther, 2010. 10(1): p. 68-76.
28. Jin, J., et al., *AMPK inhibitor Compound C stimulates ceramide production and promotes Bax redistribution and apoptosis in MCF7 breast carcinoma cells.* J Lipid Res, 2009. 50(12): p. 2389-97.
29. Yang, W. L., et al., *AMPK inhibitor compound C suppresses cell proliferation by induction of apoptosis and autophagy in human colorectal cancer cells.* J Surg Oncol, 2012. 106(6): p. 680-8.
30. Dai, R. Y., et al., *Implication of transcriptional repression in compound C-induced apoptosis in cancer cells.* Cell Death Dis, 2013. 4: p. e883.
31. Wu, Y., et al., *Compound C enhances the anticancer effect of aspirin in HER-2-positive breast cancer by regulating lipid metabolism in an AMPK-independent pathway.* Int J Biol Sci, 2020. 16(4): p. 583-597.
32. Maltman, D. J. and S. A. Przyborski, *Developments in three-dimensional cell culture technology aimed at improving the accuracy of in vitro analyses.* Biochem Soc Trans, 2010. 38(4): p. 1072-5.
33. Edmondson, R., et al., *Three-dimensional cell culture systems and their applications in drug discovery and cell-based biosensors.* Assay Drug Dev Technol, 2014. 12(4): p. 207-18
34. Langhans, S. A., *Three-Dimensional in Vitro Cell Culture Models in Drug Discovery and Drug Repositioning.* Front Pharmacol, 2018. 9: p. 6.

The invention claimed is:
1. A method for treating breast cancer or pancreatic cancer by administering to a subject in need thereof an effective amount of a compound or pharmaceutically acceptable salt or solvate thereof, selected from the group consisting of

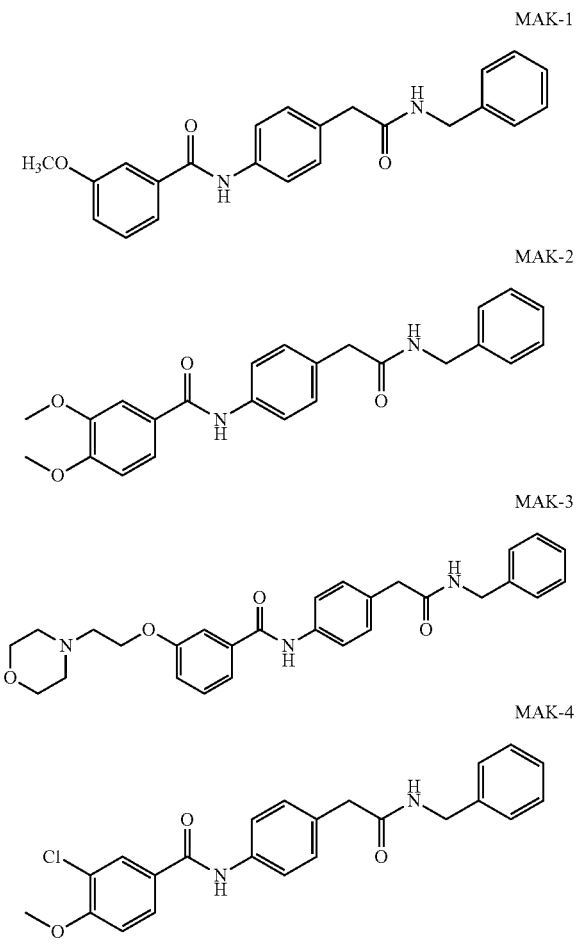

MAK-5
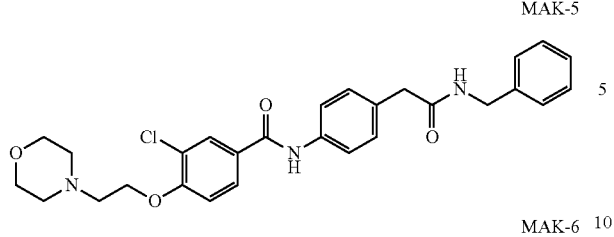

MAK-6
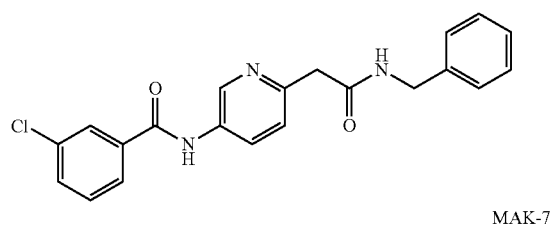

MAK-7
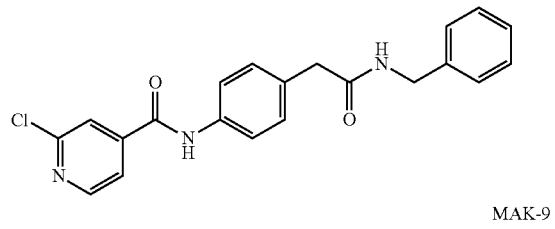

MAK-8
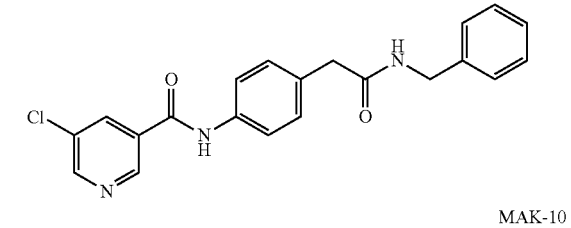

MAK-9
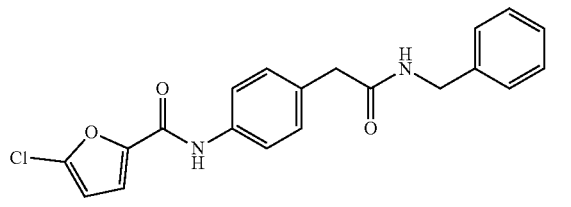

MAK-10

MAK-11
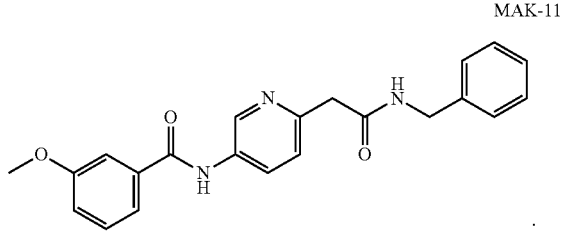

2. The method of claim 1 wherein said therapeutically effective amount of said compound is sufficient to inhibit cancer cell growth and/or proliferation.

3. The method of claim 1 wherein the compound, the pharmaceutically acceptable salt or solvate thereof is one of MAK-1
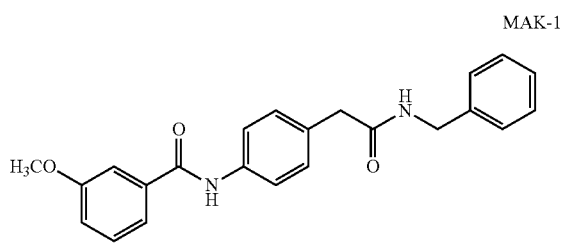

MAK-6
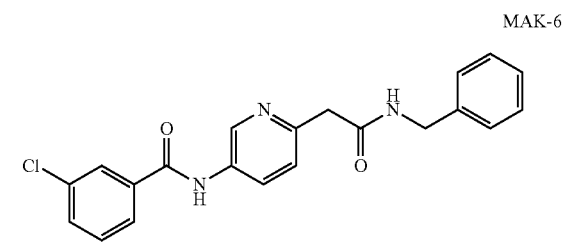

MAK-11
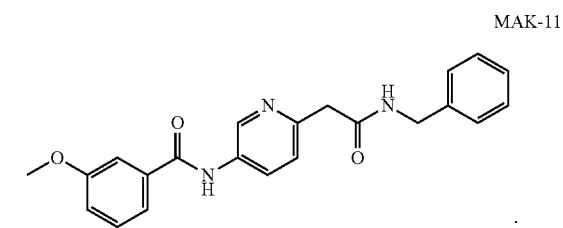

4. A method in claim 1 where wherein the compound, the pharmaceutically acceptable salt or solvate effectively decrease size, disintegrate and/or kill breast tumor aggregates.

* * * * *